United States Patent
Zhang et al.

(10) Patent No.: US 12,221,449 B2
(45) Date of Patent: Feb. 11, 2025

(54) PYRROLOPYRIMIDINE DERIVATIVE AND USE THEREOF

(71) Applicant: WUHAN HUMANWELL INNOVATIVE DRUG RESEARCH AND DEVELOPMENT CENTER LIMITED COMPANY, Hubei (CN)

(72) Inventors: Xuejun Zhang, Hubei (CN); Dabing Ye, Hubei (CN); Lie Li, Hubei (CN); Jie Shen, Hubei (CN); Xiaohua Ding, Hubei (CN); Hongna Sun, Hubei (CN); Zhe Liu, Hubei (CN); Yang Zang, Hubei (CN); Yonggang Wei, Hubei (CN)

(73) Assignee: WUHAN HUMANWELL INNOVATIVE DRUG RESEARCH AND DEVELOPMENT CENTER LIMITED COMPANY, Hubei (CN)

( * ) Notice: Subject to any disclaimer, the term of this patent is extended or adjusted under 35 U.S.C. 154(b) by 704 days.

(21) Appl. No.: 17/423,482

(22) PCT Filed: Jan. 22, 2020

(86) PCT No.: PCT/CN2020/073859
§ 371 (c)(1),
(2) Date: Jul. 16, 2021

(87) PCT Pub. No.: WO2020/156459
PCT Pub. Date: Aug. 6, 2020

(65) Prior Publication Data
US 2022/0064172 A1 Mar. 3, 2022

(30) Foreign Application Priority Data

Feb. 1, 2019 (CN) .................. 201910106140.X
Jun. 26, 2019 (CN) .................. 201910572538.2

(51) Int. Cl.
C07D 487/04 (2006.01)
A61K 31/519 (2006.01)
A61K 45/06 (2006.01)

(52) U.S. Cl.
CPC .......... *C07D 487/04* (2013.01); *A61K 31/519* (2013.01); *A61K 45/06* (2013.01)

(58) Field of Classification Search
CPC ..... C07D 487/04; A61K 31/519; A61K 45/06
See application file for complete search history.

(56) References Cited

U.S. PATENT DOCUMENTS 8,969,555 B2 * 3/2015 Beauchamp ............ A61P 25/04
544/280

FOREIGN PATENT DOCUMENTS

| EA | 025106 B1 | 11/2016 |
|---|---|---|
| EA | 028364 B1 | 11/2017 |
| JP | 2016505010 A | 2/2016 |
| JP | 2016512254 A | 4/2016 |
| WO | 2014110000 A1 | 7/2014 |
| WO | 2014143583 A1 | 9/2014 |

OTHER PUBLICATIONS

Spencer B. Jones et al., "Novel Autotaxin Inhibitors for the Treatment of Osteoarthritis Pain: Lead Optimization via Structure-Based Drug Design", ACS Medicinal Chemistry Letters, 2016, 7, pp. 857-861, DOI: 10.1021/ acsmedchemlett.6b00207.
Notice of Reasons for Refusal in Japanese Patent Application No. 2021-541309, dated Aug. 9, 2022.
Spencer B. Jones et al., "Novel Autotaxin Inhibitors for the Treatment of Osteoarthritis Pain: Lead Optimization via Structure-Based Drug Design", ACS Medicinal Chemistry Letters, 2016, 7(9), pp. 857-861.
The decision to grant a patent in Russian Patent Application No. 2021119757/04(041572), dated Sep. 6, 2022.
The Office Action in Canadian Patent Application No. 3,126,176, dated Sep. 12, 2022.
The extended European search report in European Patent Application No. 20748342.1, dated Aug. 29, 2022.
Notice of acceptance for Australian patent application No. 2020213569, dated Sep. 30, 2022.

* cited by examiner

*Primary Examiner* — Erich A Leeser

(57) ABSTRACT

Provided is a new compound capable of effectively inhibiting ATX. The compound is represented by formula I, or the compound is a tautomer, a stereoisomer, a hydrate, a solvate, a salt, or a prodrug of the compound represented by formula I. In formula (I), $R^1$ and $R^2$ are independently selected from —H or —CH$_3$, provided that: $R^1$ and $R^2$ are not —H at the same time or are not —CH$_3$ at the same time.

(I)

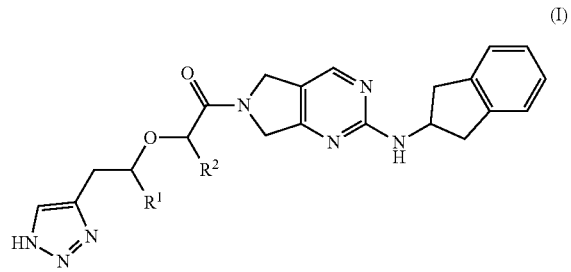

13 Claims, 2 Drawing Sheets

PYRROLOPYRIMIDINE DERIVATIVE AND USE THEREOF

FIELD

The present disclosure belongs to the field of biomedicine, specifically, the present disclosure relates to pyrrolopyrimidine derivatives, and more specifically, the present disclosure relates to pyrrolopyrimidine derivatives, methods for preparing the pyrrolopyrimidine derivatives, and use of the pyrrolopyrimidine derivatives in the preparation of medicaments.

BACKGROUND

Autotaxin (abbreviated as ATX) is a secreted glycoprotein with phosphodiesterase (PDE) activity, and it is a member of the extracellular pyrophosphatase/phosphodiesterase (ENPP) family. Thus, autotaxin is also called ENPP2. ATX also has lysophospholipase D (LysoPLD) activity, and can hydrolyze lysophosphatidylcholine (LPC) into lysophosphatidic acid (LPA) with biological activity. LPA is an intracellular lipid mediator that affects many biological and biochemical processes.

Studies have indicated that, under pathological conditions, a level of LPA can be lowered by inhibiting ATX, thereby providing therapeutic benefits for unmet clinical needs, including cancer, lymphocyte homing, chronic inflammation, neuropathic pain, fibrosis, thrombosis, and cholestatic itching, or fibrotic diseases that are induced, mediated, and/or spread through an elevated level of LPA and/or an activation of ATX.

Up-regulation of the ATX-LPA signaling pathway can be observed in various inflammatory conditions. For example, the pro-inflammatory effects of LPA include mast cell degranulation, smooth muscle cell contraction, and release of cytokine from dendritic cells. As a manifestation of its general role in inflammation, the up-regulation of the ATX-LPA signaling pathway was observed in a mouse carrageenan air pouch model, which is adopted to develop anti-inflammatory drugs, including cyclooxygenase inhibitors for arthritis (Hidenobu Kanda, Rebecca Newton, Russell Klein et al., Autotaxin, an ectoenzyme that produces lysophosphatidic acid, promotes the entry of lymphocytes into secondary lymphoid organs[J] Nature Immunology. 2008, 9(4):415-423.). In addition, a reduction of LPA in plasma and in an air pouch has been observed in a rat carrageenan air pouch model using an ATX inhibitor, which confirms the role of ATX as the main source of LPA during inflammation. As another general role in inflammatory diseases, a "synergistic effect" between LPA and lymphocyte migration chemokines has been confirmed. High ATX expression can be found in chronic inflammation sites. It has been confirmed that the homing of T-cells to lymphatic tissues is inhibited through intravenously injecting the inactivated ATX, which may be achieved by competing with endogenous ATX and exerting a dominant negative effect. In some cases, ATX facilitates the entry of lymphocytes into lymphoid organs. Therefore, ATX inhibitors can block the migration of lymphocytes into secondary lymphoid organs and are beneficial in autoimmune diseases.

In rheumatoid arthritis, it has been confirmed that ATX expression is increased in synovial fibroblasts from patients with rheumatoid arthritis (RA), and the elimination of ATX expression in mesenchymal cells (including synovial fibroblasts) results in symptom weakening in a mouse model of rheumatoid arthritis. As such, the role of autotaxin in rheumatoid arthritis has been fully established.

LPA can also up-regulate pain-related proteins through $LPA_1$, which is one of its homologous receptors. A targeted inhibition against ATX-mediated biosynthesis of LPA can serve as a mechanism to prevent neuropathic pain caused by nerve damage, such as pain associated with osteoarthritis. It has been observed that autotaxin inhibitors reduce LPA and PGE2 and also alleviate the inflammatory pain. It has also indicated through research that the targeted inhibition against ATX-mediated biosynthesis of LPA can be a new mechanism to prevent neuropathic pain caused by nerve damage.

After the inflammation subsides and the tissue damage is repaired, the tissue usually recovers to its original state. Excessive and uncontrolled tissue repair may lead to what is commonly referred to as fibrosis. Fibrosis is characterized by excessive deposition of extracellular matrix components and excessive growth of fibroblasts. Fibrosis may occur in all tissues, but it is especially common in organs that are frequently chemically and biologically damaged, including lungs, skin, digestive tract, kidneys, and liver. Fibrosis often seriously harms the normal functions of organs.

In some cases, LPA stimulates the proliferation of hepatic stellate cells while inhibiting DNA synthesis in hepatocytes. An LPA level and a serum ATX activity are elevated in patients with chronic hepatitis C. In the blood of rabbits with different liver injuries, a plasma LPA concentration and a serum ATX activity are relatively higher in carbon tetrachloride-induced liver fibrosis. The plasma LPA concentration and the serum ATX activity increase with the severity of different liver injuries.

Pulmonary fibrosis is the end-stage change of a large group of lung diseases, which are characterized by the proliferation of fibroblasts and the accumulation of a large amount of extracellular matrix accompanied by inflammatory damage and destruction of tissue structure, i.e., structural abnormality (scar formation) caused by abnormal repair after the normal alveolar tissues are damaged. When the lung damage is attributed to various causes, the interstitial tissues will secrete collagen for repair. If it is repaired excessively, i.e., the excessive proliferation of fibroblasts and the accumulation of extracellular matrix, the pulmonary fibrosis will be developed.

LPA signal has the effect of promoting fibrosis on epithelial cells, endothelial cells and fibroblasts specifically through the $LPA_1$ receptor: genetic deletion of this receptor reduces epithelial cell apoptosis, vascular leakage and fibroblast accumulation in the pulmonary fibrosis model.

Idiopathic pulmonary fibrosis (IPF) is a chronic, progressive, and fibrotic interstitial pneumonia with unknown etiology, characterized by diffuse alveolitis and alveolar structural disorders, typically revealing as ordinary interstitial pneumonia in imaging and pathologic histology. As the course of the disease progresses, the lung tissue of the patient will become thicker and harder, resulting in permanent scars, or the patient's lung looks like a honeycomb, also vividly referred to as "honeycomb lung" or "luffa lung". This chronic progressive disease will cause an irreversible and continuous decline in lung function. 50% of the patients may have an average survival time of only 2.8 years since they were diagnosed. Thus, the idiopathic pulmonary fibrosis is also referred to as "tumor-like disease." At present, the existing drug treatments have the problems such as many adverse reactions, poor therapeutic effects; and the non-drug treatments mainly include lung transplantation, but organ transplantation is expensive and limited in resources, and certain clinical risks accompanies.

There is evidence demonstrating that the proliferation and contraction of fibroblasts and extracellular matrix secretion stimulated by LPA promote fibrous proliferation in other airway diseases, such as chronic bronchitis and interstitial lung disease, as well as peribronchial fibrosis in severe asthma. LPA plays a role in fibrosis interstitial lung disease and bronchiolitis obliterans, in which collagen and myofibroblasts are both increased. Studies related to idiopathic pulmonary fibrosis (IPF) have indicated that the LPA level in patients' bronchoalveolar lavage fluid is increased. Further research on LPA1 knockout and inhibitors have revealed that LPA plays a key role in the process of lung fibrosis, which is supplemented by the investigation using cell-specific knockout mice lacking ATX in bronchial epithelial cells and macrophages. It has been indicated that the mice were less sensitive to the lung fibrosis model. The role of LPA in other fibrosis diseases (kidney and skin) is based on similar observations. The role of LPA in lung remodeling is related to the effects of LPA on both lung fibroblasts (via LPA1) and epithelial cells (via LPA2). It has been indicated that LPA2 plays a pivotal role in the activation of TGFβ in epithelial cells in the case of fibrosis disorders. The roles of LPA in remodeling and fibrosis are related to COPD, IPF and asthma, and lung remodeling, as a long-term result, will limit lung function. Finally, for the focus on lung diseases, ATX is one of the three main quantitative trait loci that seem to be associated with lung function differences in mice.

The study found that LPA concentration increases in plasma and ascites in patients with ovarian cancer at the early and late stages. The elevated LPA level and changes in expression and response of LPA receptors may be one of the causes for the onset, progression or outcome of ovarian cancer. LPA is also associated with prostate cancer, breast cancer, melanoma cancer, head and neck cancer, bowel cancer, brain cancer and thyroid cancer. LPA is involved in tumor cell proliferation and invasion of adjacent tissues, leading to metastasis. These biological and pathobiological processes are initiated by activating G protein-coupled receptors with LPA. The LPA level can be lowered by inhibiting enzymes involving in the LPA biosynthesis, such as ATX, for treatment of tumor patients.

In the process of angiogenesis, ATX and other angiogenic factors together lead to angiogenesis. The tumor can be nourished through the angiogenesis during tumor growth. Accordingly, an important starting point for cancer and tumor treatment is to inhibit the angiogenesis.

Patent Application WO2014202458A1 recites the effects of ATX-LPA signaling in different pathophysiological conditions, such as proliferative diseases, neuropathic pain, inflammation, autoimmune diseases, fibrosis, lymphocyte tracing in lymph nodes, obesity, diabetes, or embryos blood vessel formation.

At present, certain progresses in the treatments of cancer, fibrosis diseases, proliferative diseases, inflammatory diseases, autoimmune diseases, respiratory diseases, cardiovascular diseases, neurodegenerative diseases, dermatological disorders, and/or abnormal angiogenesis-related diseases have been made, but they are still insufficient. The currently marketed IPF therapeutic drugs include Pirfenidone and Nintedanib. Pirfenidone may result in liver damage (such as liver failure, jaundice), hypersensitivity reactions (such as facial swelling, laryngeal edema, dyspnea, wheezing, etc.), and severe gastrointestinal reactions, and photogenotoxicity assays demonstrated that it may cause structural abnormality of chromosomes and may cause skin cancer under light exposure. Nintedanib has adverse reactions such as diarrhea, nausea, and abdominal pain, the incidence of gastrointestinal reactions can be as high as 50%, and common adverse reactions thereof include weight loss, loss of appetite, liver damage, and bleeding, etc. Among the patients who are taking Pirfenidone and Nintedanib, the probability of discontinuation due to serious adverse events was 20.9% and 26.3%, respectively (Toby M Maher, et al. Rationale, design and objectives of two phase III, randomised, placebocontrolled studies of GLPG1690, a novel autotaxin inhibitor, in idiopathic pulmonary fibrosis (ISABELA 1 and 2)[J]. BMJ Open Respiratory Research. 2019, 21; 6(1).). The living quality of IPF patients will be severely affected, while neither Pirfenidone nor Nintedanib fails to improve the living quality of the patients in clinical trials. Although both of these two drugs may improve overall results, they can only delay the course of the disease but cannot reverse pulmonary fibrosis. In this regard, the patients with severe specific pulmonary fibrosis may not benefit therefrom. GLPG-1690, as one of the medicaments for treating IPF that is now under development and has made rapid progress, exhibits a trend of reversing the course of the disease, but it has the problems in low enzyme activity, large dosage of clinical medication, and poor medication compliance.

Therefore, the currently existing therapies are still unsatisfactory. There are still a large number of patients who are in need of new treatments with higher activity and better efficacy, which can slow down the course of the disease to a greater extent or even reverse the course of the disease, improve medication compliance, and allow more patients with idiopathic pulmonary fibrosis to benefit therefrom.

SUMMARY

The present disclosure aims to provide a compound, which can effectively inhibit ATX and can be used as an improvement or replacement of the existing medicaments or ATX inhibitors.

In a first aspect of the present disclosure, the present disclosure provides a compound, which is a compound represented by Formula I, or a mesomer, a racemate, a tautomer, a stereoisomer, a hydrate, a solvate, a salt, or a prodrug of the compound represented by Formula I,

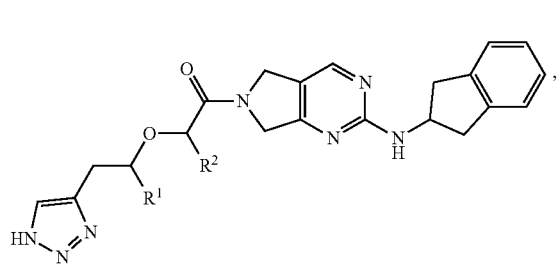

I where
$R^1$ and $R^2$ are each independently selected from —H or —CH$_3$,
provided that:
when $R^1$ and $R^2$ are not —H simultaneously; or
when $R^1$ and $R^2$ are not —CH$_3$ simultaneously.

According to embodiments of the present disclosure, the above-mentioned compound may further have at least one of the following additional technical features.

According to an embodiment of the present disclosure, R¹ is —H, and R² is —CH₃.

According to an embodiment of the present disclosure, R¹ is —CH₃, and R² is —H.

According to an embodiment of the present disclosure, the compound is one of the following compounds; or the compound is a mesomer, a racemate, a tautomer, a stereoisomer, a hydrate, a solvate, a salt, or a prodrug of the one of the following compounds:

I-1

I-2

I-1R

I-1S

I-2S

I-2R

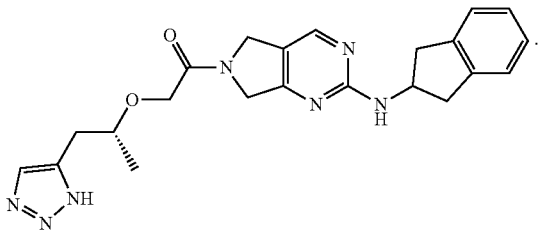

According to embodiments of the present disclosure, the salt includes pharmaceutically acceptable salts and is at least one selected from sulfuric acid, phosphoric acid, nitric acid, hydrobromic acid, hydrochloric acid, formic acid, acetic acid, propionic acid, benzenesulfonic acid, benzoic acid, phenylacetic acid, salicylic acid, alginic acid, anthranilic acid, camphoric acid, citric acid, vinyl sulfonic acid, formic acid, fumaric acid, furoic acid, gluconic acid, glucuronic acid, glutamic acid, glycolic acid, isethionic acid, lactic acid, maleic acid, malic acid, mandelic acid, mucic acid, pamoic acid, pantothenic acid, stearic acid, succinic acid, sulfanilic acid, tartaric acid, p-toluenesulfonic acid, malonic acid, 2-hydroxypropionic acid, oxalic acid, glycolic acid, glucuronic acid, galacturonic acid, citric acid, lysine, arginine, aspartic acid, cinnamic acid, p-toluenesulfonic acid, methanesulfonic acid, ethanesulfonic acid or trifluoromethanesulfonic acid. Those skilled in the art can understand that, in addition to pharmaceutically acceptable salts, other salts can also be used in the present disclosure, acting as intermediates in the purification of compounds or in the preparation of other pharmaceutically acceptable salts, or for identifying, characterizing or purifying the compounds of the present disclosure.

In a second aspect of the present disclosure, the present disclosure provides a pharmaceutical composition. According to embodiments of the present disclosure, the pharmaceutical composition includes the aforementioned compound as an active ingredient.

In a third aspect of the present disclosure, the present disclosure provides a use of the aforementioned compound or the aforementioned pharmaceutical composition in manufacture of a medicament for treating or preventing ATX-related diseases.

According to an embodiment of the present disclosure, the use may further include at least one of the following additional technical features.

According to an embodiment of the present disclosure, the ATX-related diseases include at least one selected from cancer, metabolic disease, kidney disease, liver disease, fibrosis disease, interstitial lung disease, proliferation disease, inflammatory disease, pain, autoimmune disease, respiratory disease, cardiovascular disease, neurodegenerative diseases, dermatological disorder, and/or abnormal angiogenesis-related disease.

According to an embodiment of the present disclosure, the ATX-related diseases include at least one selected from interstitial lung disease, pulmonary fibrosis, liver fibrosis, or renal fibrosis.

According to an embodiment of the present disclosure, the ATX-related diseases include idiopathic pulmonary fibrosis.

According to an embodiment of the present disclosure, the ATX-related diseases include type II diabetes and non-alcoholic steatohepatitis.

According to an embodiment of the present disclosure, the ATX-related diseases include neuropathic pain and inflammatory pain.

According to an embodiment of the present disclosure, the ATX-related diseases include pain associated with osteoarthritis.

In a fourth aspect of the present disclosure, the present disclosure provides a drug combination. According to an embodiment of the present disclosure, the drug combination includes: the aforementioned compound or the aforementioned pharmaceutical composition; and an additional drug for treating or preventing ATX-related diseases.

According to an embodiment of the present disclosure, the compound or the pharmaceutical composition of the present disclosure can be used to provide patients in need thereof with better and more effective clinical treatment drugs or regimens. According to an embodiment of the present disclosure, the present disclosure provides a series of ATX inhibitors with novel structures, better pharmacokinetic properties, better efficacy, and good druggability, capable of effectively treating ATX-related diseases or disorders.

The present disclosure further relates to a method for treating ATX-related diseases. The method includes: administering to a patient a therapeutically effective dose of a pharmaceutical formulation including the compound of the present disclosure or a pharmaceutically acceptable salt thereof.

Term Definitions and Explanations

Unless otherwise stated, the definitions of groups and terms described in the specification and claims include actual definitions, exemplary definitions, preferred definitions, definitions recorded in tables, and definitions of specific compounds in the examples, etc., which can be arbitrarily combined and integrated with each other. The group definitions and compound structures that are combined and integrated should fall within the scope of the present disclosure.

The term "pharmaceutically acceptable" means the compounds, materials, compositions and/or dosage forms that are suitable for use in contact with human and animal tissues without excess toxicity, irritation, allergic reactions or other problems or complications within the scope of reliable medical judgment, and are commensurate with a reasonable benefit/risk ratio.

The term "pharmaceutically acceptable salt" refers to a pharmaceutically acceptable salt of a non-toxic acid or base, including salts of inorganic acids and bases, as well as organic acids and bases. Salts derived from inorganic bases include, but are not limited to, metal salts formed by Al, Ca, Li, Mg, K, Na, and Zn. Salts derived from organic bases include, but are not limited to, salts of primary, secondary or tertiary amines, including organic salts formed by naturally occurring substituted or unsubstituted amines, cyclic amines, and basic ion exchange resins, for example, organic salts formed by ammonium, isopropylamine, trimethylamine, diethylamine, triethylamine, tripropylamine, diethanolamine, ethanolamine, dimethylethanolamine, 2-dimethylaminoethanol, 2-diethylaminoethanol, dicyclohexylamine, caffeine, procaine, choline, betaine, benethamine penicillin, ethylenediamine, glucosamine, methylglucamine, theobromine, triethanolamine, tromethamine, purine, piperazine, piperidine, N-ethylpiperidine, or polyamine resin. Salts derived from inorganic and organic acids include, but are not limited to, organic salts formed by sulfuric acid, phosphoric acid, nitric acid, hydrobromic acid, hydrochloric acid, formic acid, acetic acid, etc.

In addition to the pharmaceutically acceptable salts, other salts may be adopted in the present disclosure, and they can serve as intermediates in the purification of compounds or in the preparation of other pharmaceutically acceptable salts or can be used for identifying, characterizing, or purifying the compounds of the present disclosure.

The term "stereoisomer" refers to an isomer produced by a different spatial arrangement of atoms in the molecule. The definitions and rules of stereochemistry used in the present disclosure generally follow "McGraw-Hill Dictionary of Chemical Terms (1984)", S. P. Parker, Ed., McGraw-Hill Book Company, New York; and "Stereochemistry of Organic Compounds", Eliel, E. and Wilen, S., John Wiley & Sons, Inc., New York, 1994. The compound of the present disclosure may contain an asymmetry center or chiral center, and thus different stereoisomeric forms may exist. All stereoisomeric forms of the compound of the present disclosure, including, but not limited to, diastereoisomers, enantiomers, atropisomers, geometric (or conformational) isomers, and mixtures thereof such as racemic mixtures, shall be fall within the scope of the present disclosure.

Many organic compounds exist in optically active forms, i.e., they are capable of rotating a plane of plane-polarized light. When describing optically active compounds, the prefixes D and L, or R and S are used to denote the absolute configurations of the molecule with respect to one or more chiral centers. The prefixes D and L, or (+) and (−) are symbols used to specify a rotation of plane-polarized light caused by a compound, where (−) or L indicates that the compound is levorotatory, and the prefix (+) or D indicates that the compound is dextrorotatory. For a given chemical structure, these stereoisomers are identical except that these stereoisomers are mirror images of each other. The specific stereoisomers can be referred as to enantiomers, and a mixture of such isomers is called an enantiomeric mixture. A mixture of enantiomers in 50:50 is called a racemic mixture or a racemate, which may occur when there is no stereoselectivity or stereospecificity in a chemical reaction or process.

In accordance with the selection of raw materials and methods, the compound of the present disclosure may exist in the form of one of the possible isomers or a mixture thereof, for example, as a pure optical isomer, or as a mixture of isomers such as racemic isomer and diastereoisomeric mixture, depending on the number of asymmetric carbon atoms. The optically active (R)- or (S)-isomer can be prepared using chiral synthons or chiral preparations, or resolved using conventional techniques. If the compound contains a double bond, the substituents may be in E- or Z-configuration; if the compound contains a disubstituted cycloalkyl, the substituent of the cycloalkyl may has a cis- or trans-conformation.

When the bond with a chiral carbon in the formula of the present disclosure is depicted in a straight line, it should be understood that the two configurations (R) and (S) of the chiral carbon and both the resulting enantiomerically pure compound and mixture are included in the scope defined by the general formula. The diagrammatic presentation of the racemate or pure enantiomeric compound herein is from Maehr, J. Chem. Ed. 1985, 62:114-120. Unless otherwise specified, the wedge bond and the dashed bond are used to represent the absolute configuration of a stereocenter.

The compounds of the present disclosure containing asymmetrically substituted carbon atoms can be separated in an optically active form or in a racemic form. The resolution of a racemic mixture of a compound can be carried out with any of a variety of methods known in the art. For example, the methods include fractional recrystallization using chiral resolving acids, which are optically active salt-forming organic acids. For example, the suitable resolving agents for fractional recrystallization are optically active acids, such as tartaric acid, diacetyl tartaric acid, dibenzoyl tartaric acid, mandelic acid, malic acid, lactic acid or various optically active camphorsulfonic acids such as the D and L forms of β-camphorsulfonic acid. Other resolving agents suitable for fractional crystallization include α-methyl-benzylamine in a pure stereoisomeric form (for example, S and R forms or a pure diastereomeric form), 2-phenylglycinol, norephedrine, ephedrine, N-methylephedrine, cyclohexylethylamine, 1,2-diaminocyclohexane, etc. The resolution of the racemic mixture can also be carried out by eluting a column filled with an optically active resolving agent (for example, dinitrobenzoylphenylglycine). High performance liquid chromatography (HPLC) or supercritical fluid chromatography (SFC) can also be employed. The specific method, elution conditions, and the chromatographic columns can be selected by those skilled in the art according to the structures of the compounds and the experimental results. Further, pure optically active starting materials or reagents with known configuration can also be used to obtain any enantiomers or diastereomers of the compounds described in the present disclosure through stereoorganic synthesis.

Many geometric isomers of olefins, C=N double bonds, or the like may also be present in the compounds described herein, and all these stable isomers are considered in the present disclosure. When the compound described herein contains an ethylenic double bond, such a double bond includes E- and Z-geometric isomers, unless otherwise specified.

trying to separate a single tautomer, a mixture is usually produced, the physical and chemical properties of which are consistent with the mixture of compounds. The position of equilibrium depends on the intramolecularly chemical properties. For example, for many aliphatic aldehydes and ketones, such as acetaldehyde, ketonic type is dominant; and for phenols, enol type is dominant. All tautomeric forms of the compounds are included in the present disclosure.

In the examples of the present disclosure, protons may occupy two or more positions of the cyclic form of a heterocyclic ring system, for example, 1H- and 3H-imidazole, 1H-, 2H- and 4H-1,2,4-triazole, 1H- and 2H-isoindole, and 1H- and 2H-pyrazole. The tautomeric forms can be in equilibrium or sterically fixed in one form by appropriate substitution, for example:

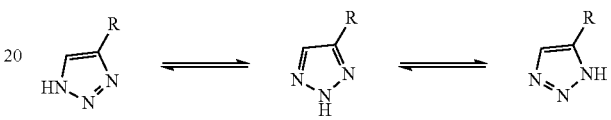

Due to resonance, a hydrogen atom on a nitrogen atom may be located on any one of the three nitrogen atoms of triazole, thus the names thereof are different, but these three forms actually represent one same compound.

As an example, the compound represented by the following formula may exist in a form of the following tautomers, all of which shall fall within the scope of the compound of the present disclosure:

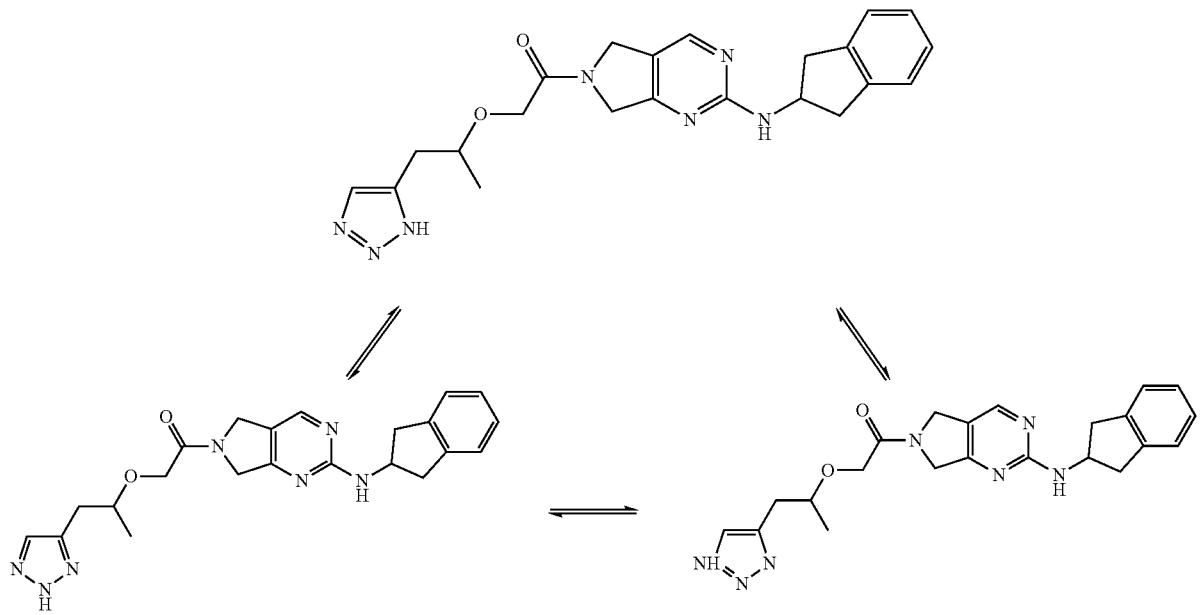

The term "tautomer" refers to an isomer of a functional group resulting from a rapid movement of an atom between two positions in a molecule. The compound of the present disclosure may exhibit tautomerism. Tautomeric compounds can be present in two or more mutually convertible species. The prototropy tautomer are resulted from a transfer of covalently bonded hydrogen atoms between two atoms. The tautomer generally exist in an equilibrium form. When The term "pharmaceutical composition" refers to a mixture of one or more of the compounds described herein or physiologically/pharmaceutically acceptable salts or prodrugs thereof and other chemical components. The other chemical components can be, for example, physiologically/pharmaceutically acceptable carriers and excipients. The pharmaceutical composition aims to facilitate the administration of the compound to an organism.

The term "solvate" refers to the compound of the present disclosure or a salt thereof including a stoichiometric or non-stoichiometric solvent bonded through an intermolecular non-covalent force. When the solvent is water, the solvate is a hydrate.

The term "prodrug" can be converted into the compound of the present disclosure having biological activity under physiological conditions or through solvolysis. The prodrug of the present disclosure is prepared by modifying the functional groups in the compound, and the modification moiety can be removed by conventional operations or in vivo, so as to obtain the parent compound. The prodrug includes a compound, which is formed by connecting a moiety to a hydroxyl group or amino group in the compound of the present disclosure. When the prodrug of the compound of the present disclosure is administered to a mammal individual, the prodrug is dissociated to form a free hydroxyl or amino group.

The compound of the present disclosure may contain an unnatural ratio of atomic isotopes on one or more of the atoms constituting the compound. For example, the compound may be labeled with a radioisotope, such as tritium ($^3H$), iodine-125 ($^{125}I$) or C-14 ($^{14}C$). The transformation of all isotopic compositions of the compounds of the present disclosure, whether radioactive or not, are included within the scope of the present disclosure.

The term "excipient" refers to a pharmaceutically acceptable inert ingredient. Examples of the "excipient" include, but not limited to, binders, disintegrants, lubricants, glidants, stabilizers, fillers, diluents, and the like. Excipients can improve the properties in term of the processing of the pharmaceutical formulation, i.e., allowing the formulation to be more suitable for direct compression by increasing fluidity and/or adhesion. Examples of typical "pharmaceutically acceptable carriers" suitable for the above formulations are: sugars such as lactose, sucrose, mannitol, and sorbitol; starches such as corn starch, tapioca starch and potato starch; cellulose and its derivatives, such as sodium carboxymethyl cellulose, ethyl cellulose, and methyl cellulose; calcium phosphates, such as dicalcium phosphate, and tricalcium phosphate; sodium sulfate; calcium sulfate; polyvinylpyrrolidone; polyvinyl alcohol; stearic acid; alkaline earth metal salts of stearic acid, such as magnesium stearate and calcium stearate; stearic acid; vegetable oils such as peanut oil, cottonseed oil, sesame oil, olive oil and corn oil; non-ionic, cationic, and anionic surfactants; ethylene glycol polymers; fatty alcohols; and grain hydrolyzed solids and other non-toxic compatible fillers, binders, disintegrants, buffers, preservatives, antioxidants, lubricants, coloring agents, and other excipients commonly used in drug formulations.

According to an embodiment of the present disclosure, the compounds of the present disclosure and/or the composition thereof can effectively inhibit ATX enzyme activity, has the advantages of better liver metabolic stability and cardiac safety, and they have better pharmacokinetic properties, a higher exposure dose in vivo, longer $T_{1/2}$, lower administration dosage and frequency, and better compliance, thereby having broad application prospects in the manufacture of medicaments for treating ATX-related diseases.

The additional aspects and advantages of the present disclosure will be partly given in the following description, and part of them will become apparent from the following description or can be understood through the implementation of the present disclosure.

DESCRIPTION OF EMBODIMENTS

Figure 1:
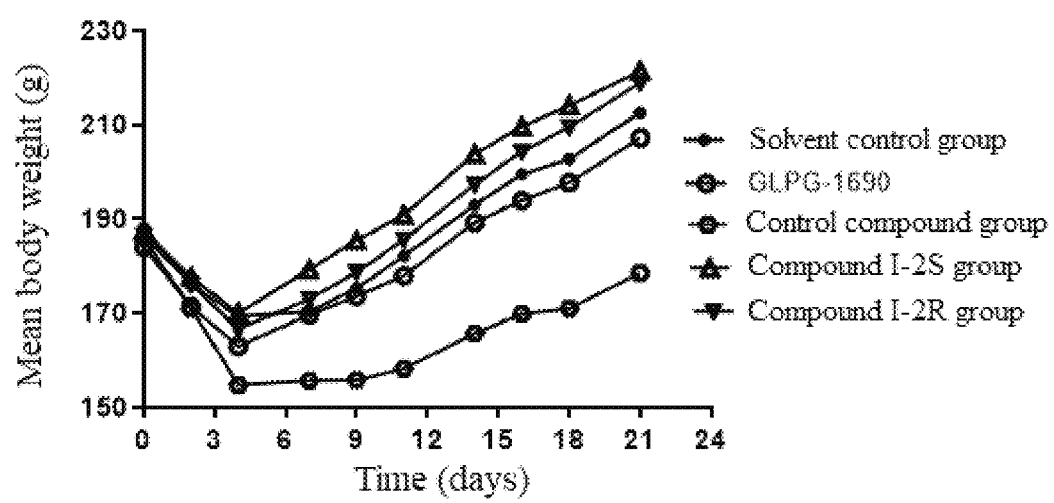
FIG. 1 is a diagram illustrating changes in animal body weight after administration according to an embodiment of the present disclosure.

The solutions of the present disclosure will be explained below in conjunction with examples. Those skilled in the art will understand that the following examples are merely used to illustrate the present disclosure, and should not be construed as limiting the scope of the present disclosure. The techniques or conditions that are not specifically indicated shall be the technology or conditions described in the literatures in the related art or in accordance with the product instructions. The reagents or instruments are all conventional products that are commercially available where the manufacturers thereof are not specified.

Unless otherwise specified, structures of the compounds of the present disclosure are identified by nuclear magnetic resonance (NMR) and/or mass spectrometry (MS). The unit of NMR shift is $10^{-6}$ (ppm). The solvent for NMR measurement is deuterated dimethyl sulfoxide, deuterated chloroform, deuterated methanol, etc., and the internal standard is tetramethylsilane (TMS).

The abbreviations in the present disclosure are defined as follows:

aq: aqueous solution dioxane: 1,4-dioxane

DMF: N,N-dimethylformamide

T3P: propylphosphonic anhydride solution, i.e., 2,4,6-tripropyl-1,3,5,2,4,6-trioxatriphosphine-2,4,6-trioxide N: equivalent concentration, for example, 1N hydrochloric acid indicates 1 mol/L solution of hydrochloric acid NMM: N-methylmorpholine DIPEA: diisopropylethylamine, i.e., N, N-diisopropylethylamine HPLC: high performance liquid chromatography SFC: supercritical fluid chromatography DMSO: dimethyl sulfoxide NADPH: reduced coenzyme II HEPES: (4-(2-hydroxyethyl)-1-piperazineethanesulfonic acid)

EGTA: ethylene glycol-bis(2-aminoethylether)-N,N,N', N'-tetraacetic acid $IC_{50}$: Half inhibitory concentration, which refers to the concentration at which half of the maximum inhibitory effect is reached.

Unless otherwise indicated, the compounds exemplified herein are named and numbered with ChemBioDraw Ultra 13.0.

Example 1: Preparation of Target Compound I-1

2-(2-(1H-1,2,3-triazol-4-yl)ethoxy)-1-(2-((2,3-dihydro-1H-inden-2-yl)amino)-5,7-dihydro-6H-pyrrolo[3,4-d]pyrimidin-6-yl)propan-1-one (Target Compound I-1)

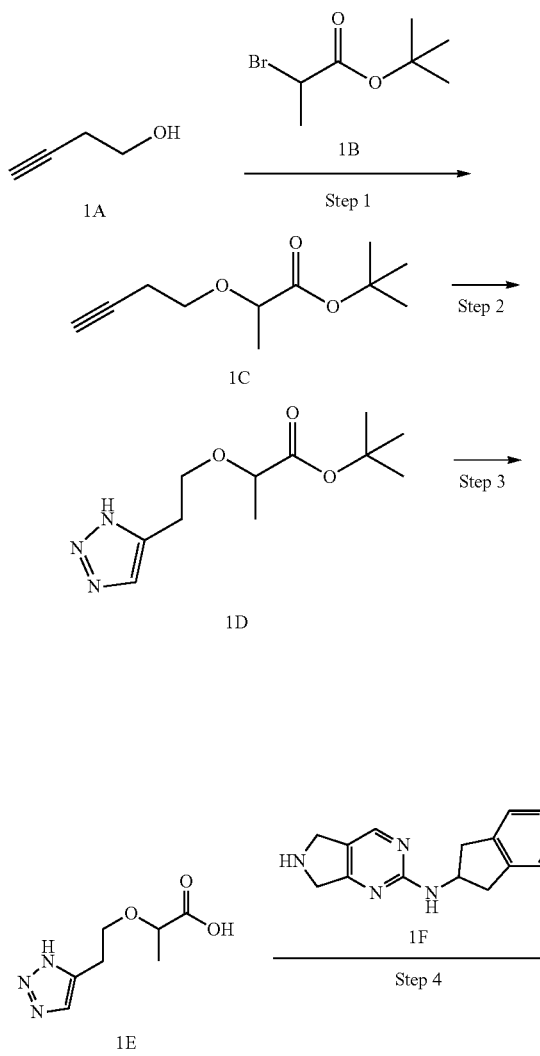

The synthetic scheme of target compound I-1 is illustrated below:

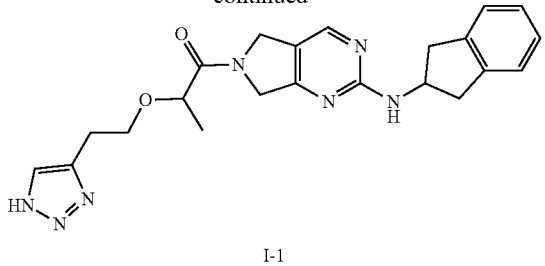

I-1

Step 1: Synthesis of tert-butyl 2-(but-3-yn-1-yloxy)propanoate (1C)

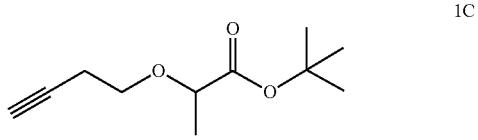

1C

At a temperature of 0° C., 3-butyn-1-ol (15 g, 214 mmol) was added to dichloromethane (300 mL), and then tetrabutylammonium hydrogen sulfate (7.27 g, 21.40 mmol), hydroxide sodium (300 mL, 3.57 mmol, 40% aq), and tert-butyl 2-bromopropionate (49.2 g, 235 mmol) were added sequentially. Then, the mixture was slowly warmed to room temperature, and stirred at room temperature for 2 h. The reaction mixture was diluted with water (300 mL), and then extracted with dichloromethane (200 mL×3). The organic layers were combined to obtain a crude product, which was separated and purified with a silica gel column (petroleum ether) to obtain a colorless oily compound, tert-butyl 2-(but-3-yn-1-yloxy)propanoate (1C) (35 g, yield 82%).

Step 2: Synthesis of tert-butyl 2-(2-(1H-1,2,3-triazol-5-yl)ethoxy)propanoate (1D)

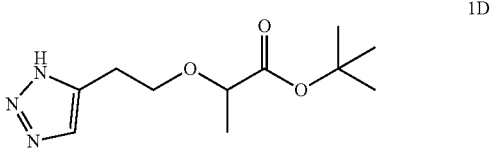 [SMILES: CC(OCCc1cnn[nH]1)C(=O)OC(C)(C)C]

1D

Under nitrogen protection, tert-butyl 2-(but-3-yn-1-yloxy)propanoate (50 g, 252 mmol) and cuprous iodide (I) (2.4 g, 12.6 mmol) were added to a mixed solution of N,N-dimethylformamide (300 mL)/methanol (30 mL), followed by adding trimethylsilyl azide (43.6 g, 378 mmol) at 0° C. The mixture was stirred at 90° C. for 18 h, then cooled to room temperature, and concentrated under reduced pressure. The residue was separated and purified with silica gel column (petroleum ether:ethyl acetate (V/V)=10:1 to 5:1) to obtain the title compound, tert-butyl 2-(2-(1H-1,2,3-triazol-5-yl)ethoxy)propanoate (1D) (40 g, 166 mmol, 65.7% yield).

LC-MS, M/Z (ESI): 242.2 (M+1)

Step 3: Synthesis of 2-(2-(1H-1,2,3-triazol-5-yl)ethoxy)propanoic acid (1E)

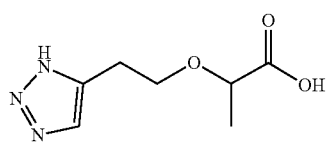

At 0° C., trifluoroacetic acid (150 mL) was added to a solution of tert-butyl 2-(2-(1H-1,2,3-triazol-5-yl)ethoxy)propanoate (50 g, 207 mmol) in dichloromethane (150 mL), and then stirred at room temperature for 2 h. The reaction mixture was concentrated to obtain a crude product 2-(2-(1H-1,2,3-triazol-5-yl)ethoxy)propanoic acid trifluoroacetate (62 g, 207 mmol, 100% yield), direct for use in a next step of reaction.

Step 4: Synthesis of 2-(2-(1H-1,2,3-triazol-4-yl)ethoxy)-1-(2-((2,3-dihydro-1H-inden-2-yl)amino)-5,7-dihydro-6H-pyrrolo[3,4-d]pyrimidin-6-yl)propan-1-one (Compound I-1)

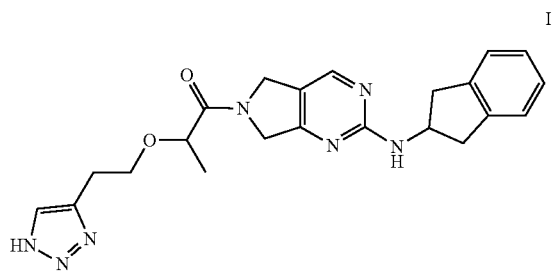

At room temperature, N-(2,3-dihydro-1H-inden-2-yl)-6,7-dihydro-5H-pyrrolo[3,4-d]pyrimidin-2-amine hydrochloride (the synthesis thereof recited in Patent Application WO2014110000A1) (7 g, 21.5 mmol) was added to DMF (40 mL), followed by sequentially adding 2-(2-(1H-1,2,3-triazol-5-yl)ethoxy)propanoic acid trifluoroacetate (9.66 g, 32.3 mmol) and DIEA (27.8 g, 215 mmol). 2,4,6-tripropyl-1,3,5,2,4,6-trioxatriphosphine-2,4,6-trioxide (10.3 g, 32.3 mmol, 50% DMF solution) was added at 0° C. Then, the mixture was slowly warmed to room temperature and stirred at room temperature for 12 h. Completion of the reaction was detected by TLC, the reaction solution was poured in the distilled water (150 mL) while stirring, and the precipitated solid was beaten with acetonitrile (50 mL) and filtered to obtain a solid compound, 2-(2-(1H-1,2,3-triazol-4-yl)ethoxy)-1-(2-((2,3-dihydro-1H-inden-2-yl)amino)-5,7-dihydro-6H-pyrrolo[3,4-d]pyrimidin-6-yl)propan-1-one (8.1 g, 90% yield).

$^1$H NMR (400 MHz, CDCl$_3$) δ 8.17 (m, 1H), 7.45 (s, 1H), 7.19-7.09 (m, 4H), 5.53 (s, 1H), 4.73-4.51 (m, 5H), 4.18-4.15 (m, 1H), 3.73-3.68 (m, 2H), 3.53-3.29 (m, 2H), 3.03-2.77 (m, 4H), 1.19-1.15 (m, 3H).

LC-MS, M/Z (ESI): 420.3 (M+1).

Example 2: Preparation of Target Compound I-1R (R)-2-(2-(1H-1,2,3-triazol-4-yl)ethoxy)-1-(2-((2,3-dihydro-1H-inden-2-yl)amino)-5,7-dihydro-6H-pyrrolo[3,4-d]pyrimidin-6-yl)propan-1-one (Target Compound I-1R)

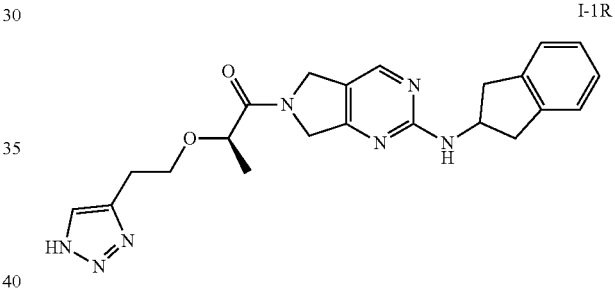

The synthesis scheme of the target compound I-1R is illustrated as below:

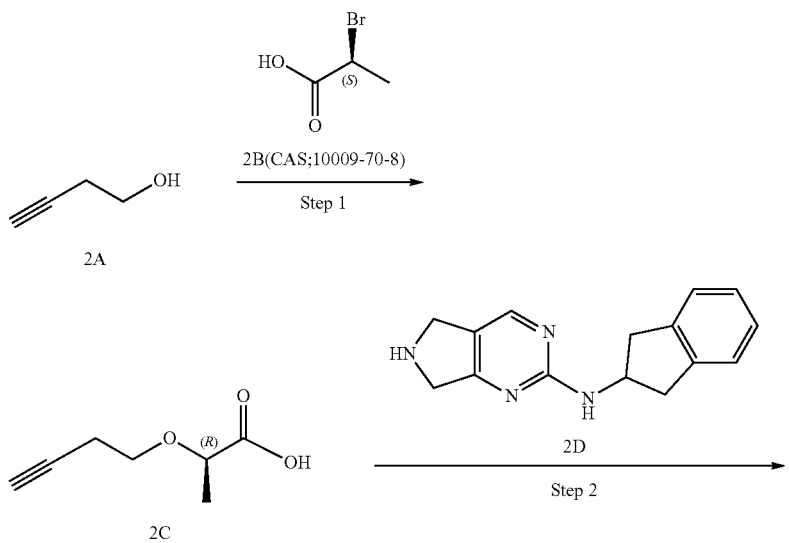

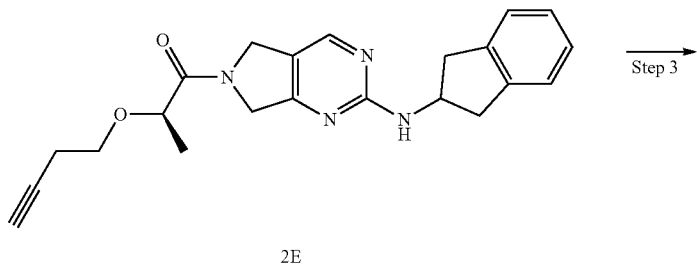

2E

→ Step 3

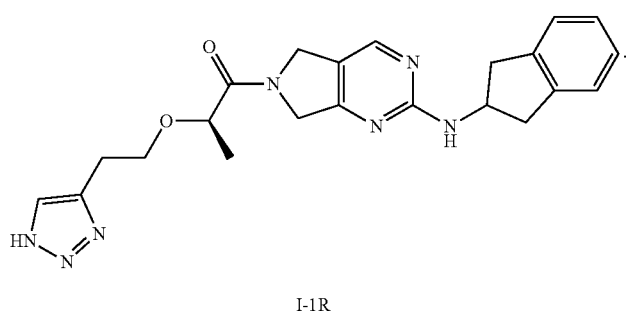

I-1R

Step 1: Synthesis of (R)-2-(but-3-yn-1-yloxy)propanoic acid (2C)

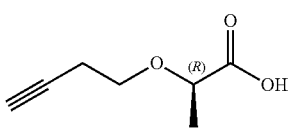

2C 3-butyn-1 alcohol (350 mg, 5 mmol) was added to DMF (5 mL), cooled to 0° C., followed by adding NaH (400 mg, 10 mmol, 60%), stirring for 30 min. Then, a raw material (S)-2-bromopropionic acid (700 mg, 4.5 mmol) was added, followed by stirring at 0° C. for 5 h. Then, the reaction solution was added with water (10 mL) at 0° C., and pH was adjusted to 1-2 with hydrochloric acid (1N). The reaction solution was extracted with ethyl acetate (20 mL×3); and the organic phases were combined, dried with anhydrous sodium sulfate, filtered, and concentrated. The residue was separated and purified with a silica gel column (petroleum ether:ethyl acetate (V/V)=1:1) to obtain the title compound as a light-yellow liquid (R)-2-(but-3-yn-1-yloxy)propanoic acid (2C) (390 mg, 60% yield).

Step 2: Synthesis of (R)-2-(but-3-yn-1-yloxy)-1-(2-((2,3-dihydro-1H-inden-2-yl)amino)-5,7-dihydro-6H-pyrrolo[3,4-d]pyrimidin-6-yl)propan-1-one (2E)

2E

The raw material (R)-2-(but-3-yn-1-yloxy)propanoic acid (56 mg, 4 mmol) was added to DMF (2 mL) at room temperature, followed by sequentially adding raw materials N-(2,3-dihydro-1H-inden-2-yl)-6,7-dihydro-5H-pyrrolo[3,4-d]pyrimidin-2-amine (100 mg, 4 mmol), 2-(7-azabenzotriazol-1-yl)-N,N,N',N'-tetramethyluronium hexafluorophosphate (180 mg, 4.4 mmol), and triethylamine (82 mg, 8 mmol). Then, the reaction solution was heated to 50° C. and stirred for 15 h. The reaction solution was cooled to room temperature, added with water (6 mL), and extracted with ethyl acetate (5 mL×3). The organic phases were combined, dried with anhydrous sodium sulfate, and concentrated. The residue was separated and purified with a silica gel column (dichloromethane:methanol (V/V)=10:1) to obtain the title compound, which was a yellow solid of (R)-2-(but-3-yn-1-yloxy)-1-(2-((2,3-dihydro-1H-inden-2-yl)amino)-5,7-dihydro-6H-pyrrolo[3,4-d]pyrimidin-6-yl)propan-1-one (80 mg, 53.9%).

Step 3: Synthesis of (R)-2-(2-(1H-1,2,3-triazol-4-yl)ethoxy)-1-(2-((2,3-dihydro-1H-inden-2-yl)amino)-5,7-dihydro-6H-pyrrolo[3,4-d]pyrimidin-6-yl)propan-1-one (compound I-1R)

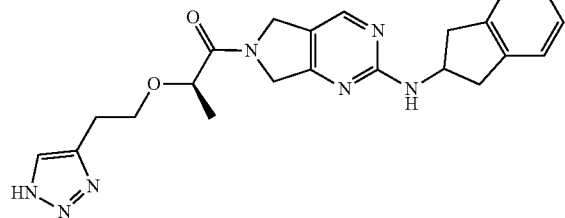

I-1R

At room temperature, the raw material (R)-2-(but-3-yn-1-yloxy)-1-(2-((2,3-dihydro-1H-inden-2-yl)amino)-5,7-dihydro-6H-pyrrolo[3,4-d]pyrimidin-6-yl)propan-1-one (80 mg, 0.21 mmol) was added to DMF (2 mL) and methanol (0.5 mL), followed by sequentially adding trimethylsilylazide (37 mg, 0.32 mmol) and cuprous iodide (5 mg, 0.025 mmol) under nitrogen protection. The reaction solution was heated to 80° C. and stirred for 15 h. The reaction solution was then cooled to room temperature, added with water (8 mL), and extracted with ethyl acetate (5 mL×3). The organic phases were combined, dried with anhydrous sodium sulfate, and concentrated. The residue was separated and purified with a silica gel column (dichloromethane:methanol (V/V)=10:1) to obtain the title compound, a yellow solid of (R)-2-(2-(1H-1,2,3-triazol-4-yl)ethoxy)-1-(2-((2,3-dihydro-1H-inden-2-yl)amino)-5,7-dihydro-6H-pyrrolo[3,4-d]pyrimidin-6-yl)propan-1-one (8 mg, 8.9%).

$^1$H NMR (400 MHz, DMSO-d6) δ 8.31 (d, 1H), 7.61 (s, 1H), 7.57 (s, 1H), 7.22 (m, 2H), 7.16 (m, 2H), 4.69-4.61 (m, 4H), 4.55-4.53 (m, 1H), 4.30-4.28 (m, 1H), 3.68-3.64 (m, 2H), 3.33-3.17 (m, 2H), 2.91-2.85 (m, 4H), 1.28-1.19 (m, 3H).

LC-MS, M/Z (ESI): 420.2(M+1)

Example 3: Preparation of Target Compound I-1R and Target Compound I-1S (R)-2-(2-(1H-1,2,3-triazol-4-yl)ethoxy)-1-(2-((2,3-dihydro-1H-inden-2-yl)amino)-5,7-dihydro-6H-pyrrolo[3,4-d]pyrimidin-6-yl)propan-1-one (target compound I-1R)

(S)-2-(2-(1H-1,2,3-triazol-4-yl)ethoxy)-1-(2-((2,3-dihydro-1H-inden-2-yl)amino)-5,7-dihydro-6H-pyrrolo[3,4-d]pyrimidin-6-yl)propan-1-one (target compound I-1S)

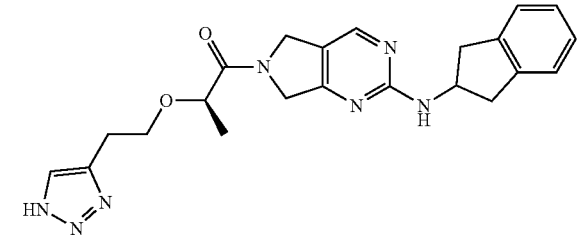

I-1R

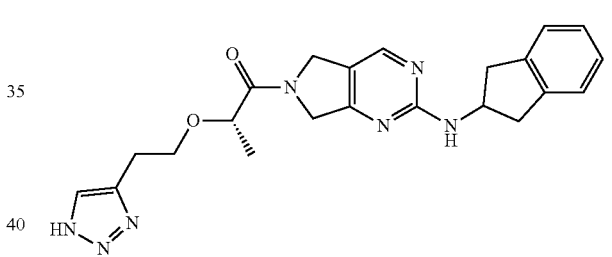

I-1S

The target compounds were obtained by SFC separation.

The racemate 2-(2-(1H-1,2,3-triazol-4-yl)ethoxy)-1-(2-((2,3-dihydro-1H-inden-2-yl)amino)-5,7-dihydro-6H-pyrrolo[3,4-d]pyrimidin-6-yl)propan-1-one (10.1 g, 24.1 mmol) was separated by SFC under the following separation conditions: column type: Chiralpak IC-350*4.6 mm, 3 μm; mobile phase: mobile phase A was $CO_2$, mobile phase B was 40% ethanol (containing 0.05% diethylamine); gradient elution: 40% ethanol in $CO_2$ (containing 0.05% diethylamine); flow rate: 3 mL/min; wavelength: 220 nm; column temperature: 35° C.; back pressure: 100 Bar. Obtained were a single isomer (R)-2-(2-(1H-1,2,3-triazol-4-yl)ethoxy)-1-(2-((2,3-dihydro-1H-inden-2-yl)amino)-5,7-dihydro-6H-pyrrolo[3,4-d]pyrimidin-6-yl)propan-1-one (target compound I-1R) (3.51 g, 100% ee, yield 34.7%), and a single isomer (S)-2-(2-(1H-1,2,3-triazol-4-yl)ethoxy)-1-(2-((2,3-dihydro-1H-inden-2-yl)amino)-5,7-dihydro-6H-pyrrolo[3,4-d]pyrimidin-6-yl)propan-1-one (target compound I-1S) (3.8 g, 97% ee, yield 37.6%).

Through chiral HPLC comparison, it was determined that two absolute configurations of the compound were obtained by SFC resolution.

Target Compound I-1R:

¹H NMR (400 MHz, DMSO-d6) δ 14.7 (bs, 1H), 8.32 (bs, 0.6H), 8.27 (bs, 0.4H), 7.67 (bs, 1H), 7.55 (t, J=12.0 Hz, 1H), 7.21-7.13 (m, 4H), 4.72-4.59 (m, 3H), 4.55-4.49 (m, 1H), 4.45-4.44 (m, 1H), 4.33-4.27 (m, 1H), 3.70-3.64 (m, 2H), 3.28-3.18 (m, 2H), 2.93-2.85 (m, 4H), 1.27 (dd, J=8.0, 4.0 Hz, 3H).

LC-MS, M/Z (ESI): 420.3 (M+1).

Retention time: 2.82 min

Target compound I-1S:

¹H NMR (400 MHz, DMSO-d6) δ 14.5 (bs, 1H), 8.32 (bs, 0.6H), 8.27 (bs, 0.4H), 7.63 (bs, 1H), 7.55 (t, J=12.0 Hz, 1H), 7.22-7.13 (m, 4H), 4.72-4.59 (m, 3H), 4.54-4.49 (m, 1H), 4.45-4.44 (m, 1H), 4.33-4.27 (m, 1H), 3.68-3.64 (m, 2H), 3.32-3.22 (m, 2H), 2.92-2.87 (m, 4H), 1.27 (dd, J=8.0, 4.0 Hz, 3H).

LC-MS, M/Z (ESI): 420.3 (M+1).

Retention time: 4.48 min

Example 4: Preparation of Target Compound I-2

2-((1-(1H-1,2,3-triazol-5-yl)propan-2-yl)oxy)-1-(2-((2,3-dihydro-1H-inden-2-yl)amino)-5,7-dihydro-6H-pyrrolo[3,4-d]pyrimidin-6-yl)ethan-1-one (Target Compound I-2)

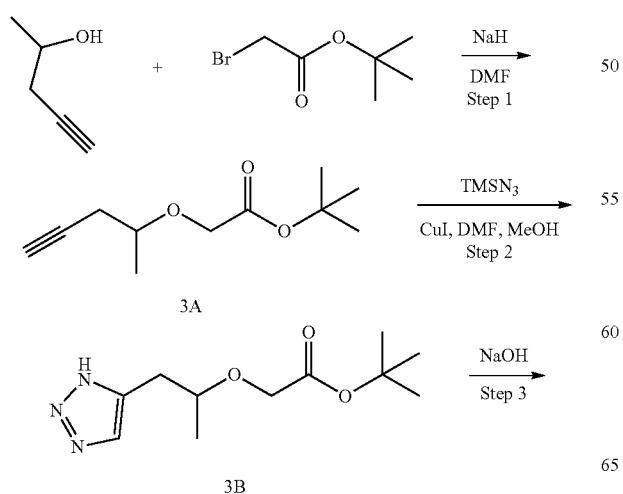

The synthesis scheme of target compound I-2 is illustrated below:

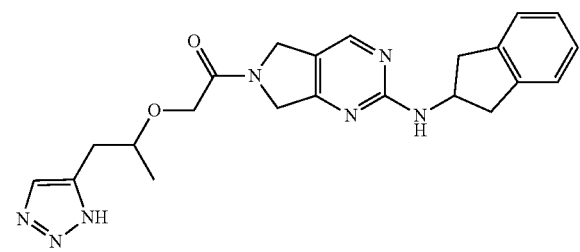

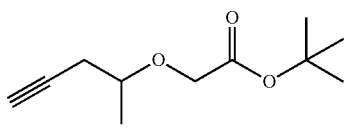

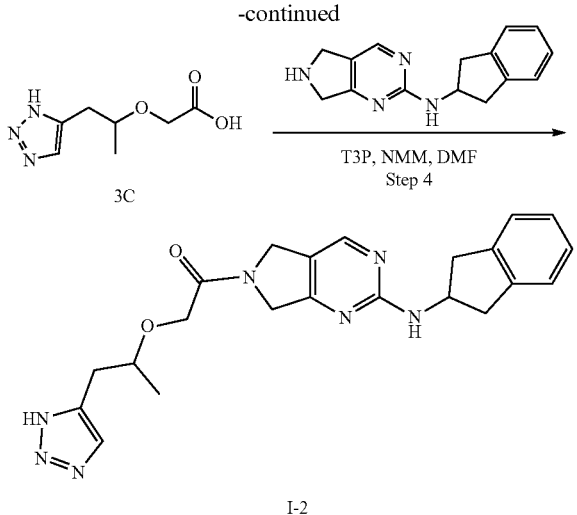

Step 1: Synthesis of tert-butyl 2-(pent-4-yn-2-yloxy)acetate (3A)

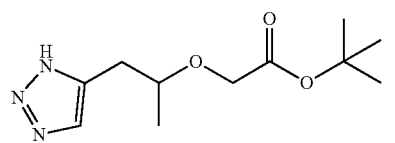

A raw material, 4-pentyne-2-ol (84.0 g, 1.0 mol), was added into 1,000 mL of dry tetrahydrofuran and cooled to 0° C., 60% NAH (80.0 g, 2.0 mol) wad added, the mixture was stirred for 30 min, a raw material t-butyl bromoacetate (234.0 g, 1.2 mol) was added at 0° C., the resulting mixture was naturally warmed to room temperature and stirred for 16 h. The reaction solution was added with water (2,000 mL) at 0° C., pH was adjusted to 1-2 with 1N hydrochloric acid, and extracted with ethyl acetate (2,000 mL×3). The organic phases were combined, dried with anhydrous sodium sulfate, filtered, and concentrated. The residue was separated and purified with a silica gel column (petroleum ether:ethyl acetate (V/V)=3:1) to obtain the title compound as a light-yellow liquid, tert-butyl 2-(pent-4-yn-2-yloxy)acetate (3A) (180 g, yield 65%).

Step 2: Synthesis of tert-butyl 2-((1-(1H-1,2,3-triazol-5-yl)propan-2-yl)oxy)acetate (3B)

The raw material, tert-butyl 2-(pent-4-yn-2-yloxy)acetate (40.0 g, 0.2 mol), was added to 400 mL of DMF and 50 mL of methanol at room temperature. Under nitrogen protection, trimethylsilyl azide (34.6 g, 0.3 mol) and cuprous iodide (8 g, 0.4 mol) were added, respectively. The reaction solution was heated to 90° C. and stirred for 15 h. The reaction solution was cooled to room temperature, then added with water (1,000 mL), and extracted with ethyl acetate (1200 mL×3). The organic phases were combined, dried with anhydrous sodium sulfate, and concentrated. The residue was separated and purified by a silica gel column (petroleum ether:ethyl acetate (V/V)=1:1) to obtain the title compound, a yellow liquid of tert-butyl 2-((1-(1H-1,2,3-triazol-5-yl)propan-2-yl)oxy)acetate (26.0 g, 53%).

Step 3: Synthesis of 2-((1-(1H-1,2,3-triazol-5-yl)propan-2-yl)oxy)acetic acid (3C)

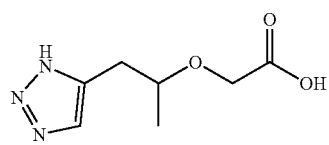

3C

At room temperature, the raw material tert-butyl 2-((1-(1H-1,2,3-triazol-5-yl)propan-2-yl)oxy)acetate (26.0 g, 0.11 mol) was added to 300 mL of DMF and 100 mL of water, and then NaOH (8.6 g, 0.22 mol) was added. The mixture was stirred at room temperature for 40 h, and then added with water (300 mL). The reaction solution was extracted with ethyl acetate (150 mL×3), and the aqueous phase was concentrated. The residue was separated and purified by a silica gel column (dichloromethane:methanol (V/V)=5:1) to obtain the title compound, a yellow liquid of 2-((1-(1H-1,2,3-triazol-5-yl)propan-2-yl)oxy)acetic acid (20 g, 85%).

Step 4: Synthesis of 2-((1-(1H-1,2,3-triazol-5-yl)propan-2-yl)oxy)-1-(2-((2,3-dihydro-1H-inden-2-yl)amino)-5,7-dihydro-6H-pyrrolo[3,4-d]pyrimidin-6-yl)ethan-1-one (Target Compound I-2)

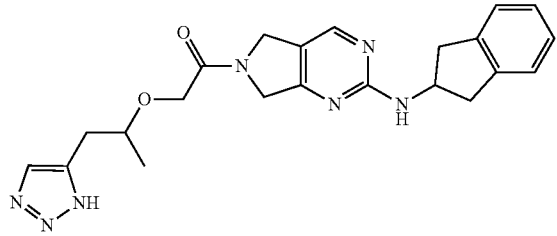

I-2

The raw material 2-((1-(1H-1,2,3-triazol-5-yl)propan-2-yl)oxy)acetic acid (20 g, 0.11 mol) was added into 400 mL of DMF at room temperature. N-(2,3-dihydro-1H-inden-2-yl)-6,7-dihydro-5H-pyrrolo[3,4-d] pyrimidin-2-amine (the synthesis thereof recited in Patent Application WO201411000A1) (12 g, 47.6 mmol), T3P (45.4 g, 71.4 mmol, 50% ethyl acetate solution), and NMM (24 g, 238 mmol) were added at 0° C. The mixture was naturally warmed to room temperature, and then stirred for 16 h. The reaction solution was filtered. The filtrate was added with water (300 mL) and extracted with ethyl acetate (1500 mL×3). The organic phases were combined, dried with anhydrous sodium sulfate, and concentrated. The residue was separated and purified with a silica gel column (dichloromethane:methanol (V/V)=10:1) to obtain the title compound, a yellow solid of 2-((1-(1H-1,2,3-triazol-5-yl)propan-2-yl)oxy)-1-(2-((2,3-dihydro-1H-inden-2-yl)amino)-5,7-dihydro-6H-pyrrolo[3,4-d]pyrimidin-6-yl)ethan-1-one (19.3 g, 92%).

$^1$H NMR (400 MHz, DMSO-d6) δ 8.30 (d, 1H), 7.64 (b, 1H), 7.57 (t, 1H), 7.22-7.20 (m, 2H), 7.16-7.12 (m, 2H), 4.65-4.59 (m, 3H), 4.52 (s, 1H), 4.42 (s, 1H), 4.25-4.17 (m, 2H), 3.87-3.81 (m, 1H), 3.27-3.21 (m, 2H), 2.90-2.85 (m, 4H), 1.19 (t, 3H)

LC-MS, M/Z (ESI): 420.2(M+1)

Example 5: Preparation of Target Compound I-2S (S)-2-((1-(1H-1,2,3-triazol-5-yl)propan-2-yl)oxy)-1-(2-((2,3-dihydro-1H-inden-2-yl) amino)-5,7-dihydro-6H-pyrrolo[3,4-d]pyrimidin-6-yl)ethan-1-one (Target Compound I-2S)

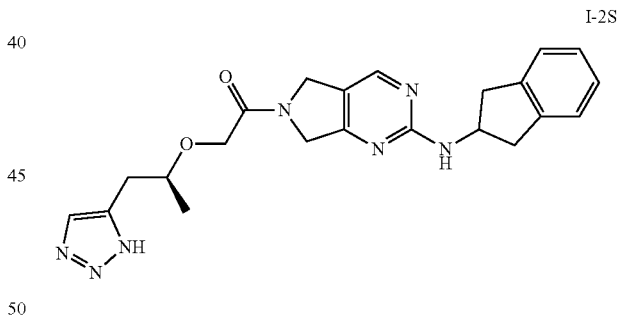

I-2S

The synthesis scheme of target compound I-2S is illustrated below:

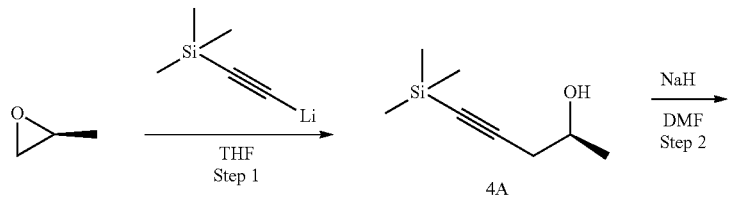

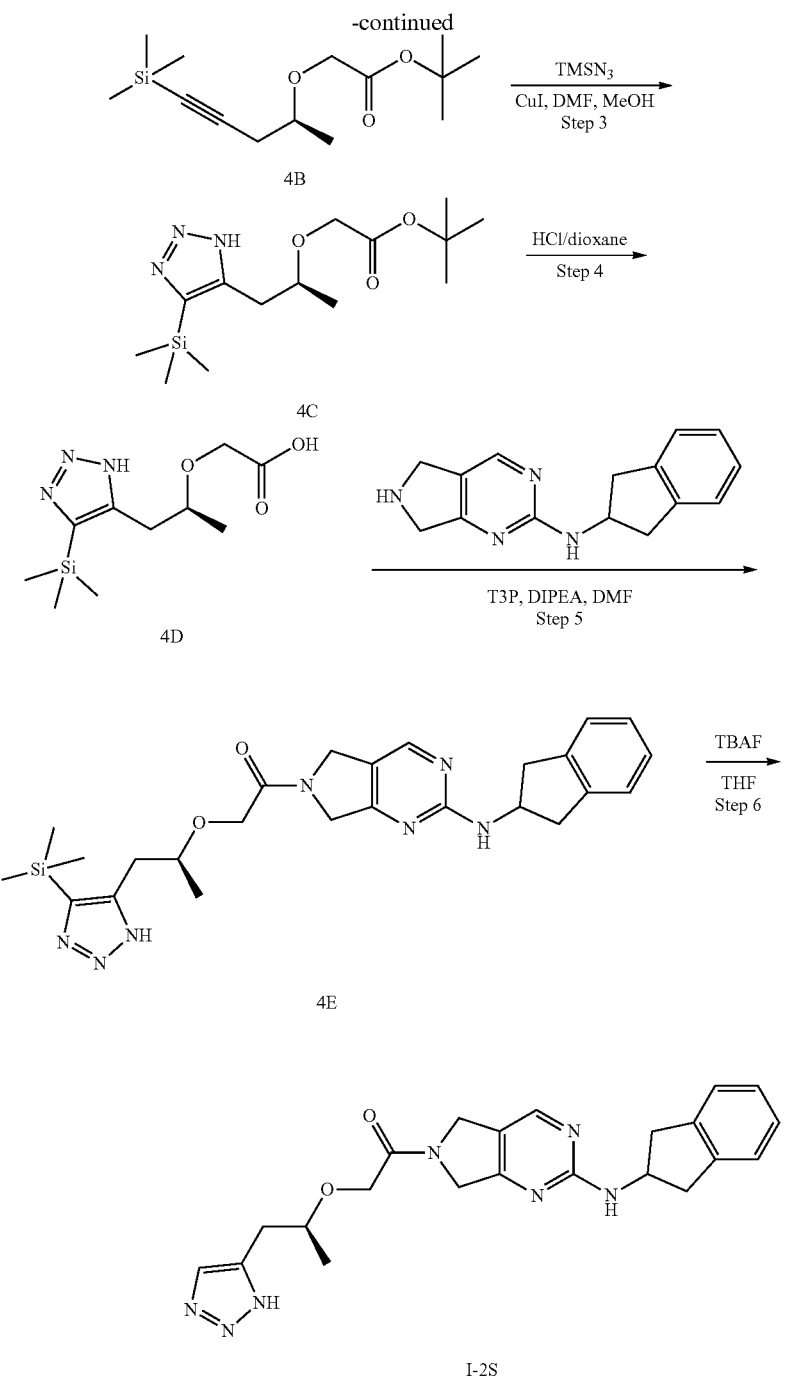

Step 1: Synthesis of (S)-5-(trimethylsilyl)pent-4-yn-2-ol (4A)

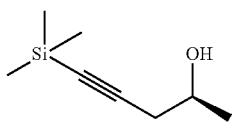

A tetrahydrofuran solution of lithium (trimethylsilyl) acetylide (0.5 M, 52 mL) was added into a three-necked flask and cooled to −70° C. under the nitrogen protection, followed by adding tetrahydrofuran solution of boron trifluoride (50%, 2.4 mL) and slowly adding (S)-propylene oxide (1.5 g) dropwise. After the dropwise addition, the mixture was stirred while holding the temperature for 1 hour, and then a saturated ammonium chloride aqueous solution (10 mL) was added to quench the reaction. The solution, after being heated to room temperature, was separated into an organic phase and an aqueous phase. The organic phase was dried and concentrated to obtain a crude product (2.0 g) which was directly used for the next step of reaction.

Step 2: Synthesis of tert-butyl (S)-2-((5-(trimethylsilyl)pent-4-yn-2-yl)oxy)acetate (4B)

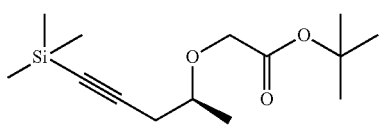

4B

The raw material (S)-5-(trimethylsilyl)pent-4-yn-2-ol (2.0 g, 12.8 mmol) was added to 10 mL of dry tetrahydrofuran, cooled to 0° C., added with 60% NaH (0.49 g, 12.8 mmol), stirred for 30 min, and then added with the raw material tert-butyl 2-bromoacetate (3.0 g, 15.4 mmol) at 0° C. The mixture was warmed to room temperature naturally and stirred for 16 h. The reaction solution was added with water (20 mL) at 0° C., pH was adjusted to pH 1-2 with 1N hydrochloric acid, and extracted with ethyl acetate (20 mL×3). The organic phases were combined, dried with anhydrous sodium sulfate, filtered, and concentrated. The residue was separated and purified with a silica gel column (petroleum ether:ethyl acetate (V/V)=3:1) to obtain the title compound, a light-yellow liquid of tert-butyl (S)-2-((5-(trimethylsilyl)pent-4-yn-2-yl)oxy)acetate (4B) (2.1 g, yield 60.7%).

Step 3: Synthesis of tert-butyl (S)-2-((1-(4-(trimethylsilyl)-1H-1,2,3-triazol-5-yl)propan-2-yl)oxy)acetate (4C)

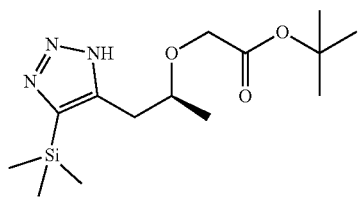

4C

At room temperature, the raw material tert-butyl (S)-2-((5-(trimethylsilyl)pent-4-yn-2-yl)oxy)acetate (1.0 g, 3.7 mmol) was added to 10 mL of DMF and 5 mL of methanol, followed by adding trimethylsilyl azide (0.64 g, 5.5 mmol) and cuprous iodide (0.14 g, 0.74 mmol) under nitrogen protection, respectively. The reaction was heated to 90° C. and stirred for 15 h. The reaction solution was cooled to room temperature, added with water (50 mL), and extracted with ethyl acetate (20 mL×3). The organic phases were combined, dried with anhydrous sodium sulfate, and concentrated. The residue was separated and purified with a silica gel column (petroleum ether:ethyl acetate (V/V)=1:1) to obtain the title compound, a yellow liquid of tert-butyl (S)-2-((1-(4-(trimethylsilyl)-1H-1,2,3-triazol-5-yl)propan-2-yl)oxy)acetate (0.6 g, 51.8%).

Step 4: Synthesis of (S)-2-((1-(4-(trimethylsilyl)-1H-1,2,3-triazol-5-yl)propan-2-yl)oxy)acetic acid (4D)

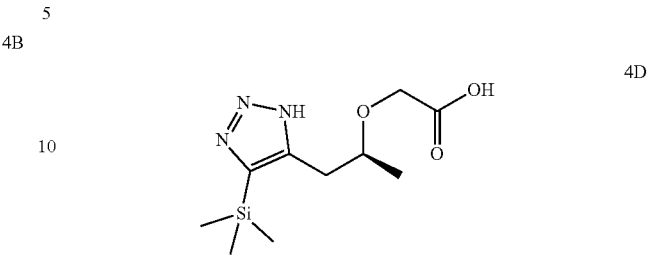

4D

At room temperature, the raw material tert-butyl (S)-2-((1-(4-(trimethylsilyl)-1H-1,2,3-triazol-5-yl)propan-2-yl)oxy)acetate (0.6 g, 1.9 mmol) was added to a hydrogen chloride solution of 1,4-dioxane (4 M, 10 mL), stirred at room temperature for 2 h, and concentrated to dryness to obtain a crude product of (S)-2-((1-(4-(trimethylsilyl)-1H-1,2,3-triazol-5-yl)propan-2-yl)oxy)acetic acid (0.5 g, 100%) which was used directly in the next step of reaction.

Step 5: Synthesis of (S)-1-(2-((2,3-dihydro-1H-inden-2-yl)amino)-5,7-dihydro-6H-pyrrolo[3,4-d]pyrimidin-6-yl)-2-((1-(4-(trimethylsilyl)-1H-1,2,3-triazol-5-yl)propan-2-yl)oxy)ethan-1-one (4E)

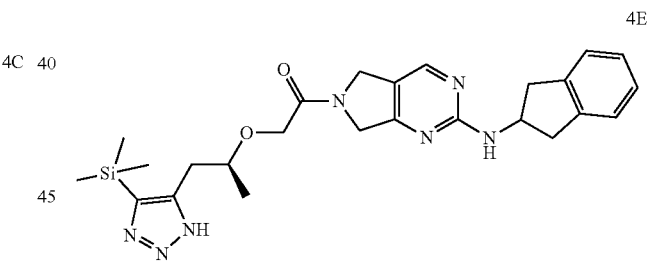

4E

The raw material (S)-2-((1-(4-(trimethylsilyl)-1H-1,2,3-triazol-5-yl)propan-2-yl)oxy)acetic acid (0.5 g, 1.9 mmol) was added to 4 mL of DMF, followed by adding N-(2,3-dihydro-1H-inden-2-yl)-6,7-dihydro-5H-pyrrolo[3,4-d]pyrimidine-2-amine (0.7 g, 2.1 mmol), T3P (1.5 g, 2.3 mmol, 50% DMF solution), and diisopropylethylamine (0.5 g, 3.8 mmol) at 0° C. The mixture was naturally warmed to room temperature and stirred for 16 h. The reaction solution was filtered, and the filtrate was added with water (30 mL) and extracted with ethyl acetate (15 mL×3). The organic phases were combined, dried with anhydrous sodium sulfate, and concentrated to obtain the crude product, (S)-1-(2-((2,3-dihydro-1H-inden-2-yl)amino)-5,7-dihydro-6H-pyrrolo[3,4-d]pyrimidin-6-yl)-2-((1-(4-(trimethylsilyl)-1H-1,2,3-triazol-5-yl)propan-2-yl)oxy)ethan-1-one (0.3 g).

Step 6: Synthesis of (S)-2-((1-(1H-1,2,3-triazol-5-yl)propan-2-yl)oxy)-1-(2-((2,3-dihydro-1H-inden-2-yl)amino)-5,7-dihydro-6H-pyrrolo[3,4-d]pyrimidin-6-yl)ethan-1-one (Target Compound I-2S)

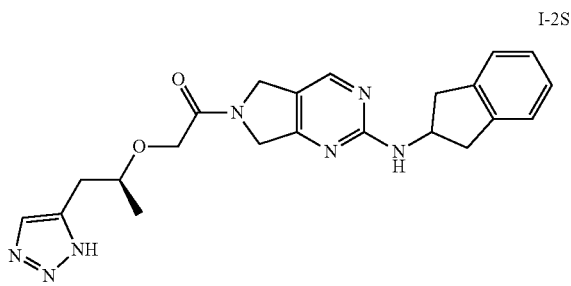

I-2S

The crude product (S)-1-(2-((2,3-dihydro-1H-inden-2-yl)amino)-5,7-dihydro-6H-pyrrolo[3,4-d]pyrimidin-6-yl)-2-((1-(4-(trimethylsilyl)-1H-1,2,3-triazol-5-yl)propan-2-yl)oxy)ethan-1-one (0.3 g) was added to tetrahydrofuran (10 mL), followed by adding tetrabutylammonium fluoride trihydrate (0.4 g, 1.2 mmol). The mixture was stirred at room temperature for 5 h, added with water (20 mL), and extracted with ethyl acetate (20 mL×3). The organic phases were combined, dried with anhydrous sodium sulfate, and concentrated. The residue was separated by preparative chromatography and lyophilized to obtain (S)-2-((1-(1H-1,2,3-triazol-5-yl)propan-2-yl)oxy)-1-(2-((2,3-dihydro-1H-inden-2-yl)amino)-5,7-dihydro-6H-pyrrolo[3,4-d]pyrimidin-6-yl)ethan-1-one (68.3 mg, two-step yield 8.4%).

$^1$H NMR (400 MHz, DMSO-d6) δ 8.30 (d, 1H), 7.64 (b, 1H), 7.57 (t, 1H), 7.22-7.20 (m, 2H), 7.16-7.12 (m, 2H), 4.65-4.59 (m, 3H), 4.52 (s, 1H), 4.42 (s, 1H), 4.25-4.17 (m, 2H), 3.87-3.81 (m, 1H), 3.27-3.21 (m, 2H), 2.90-2.85 (m, 4H), 1.19 (t, 3H)

LC-MS, M/Z (ESI): 420.4(M+1)

Example 6: Preparation of Target Compound I-2R (R)-2-((1-(1H-1,2,3-triazol-5-yl)propan-2-yl)oxy)-1-(2-((2,3-dihydro-1H-inden-2-yl)amino)-5,7-dihydro-6H-pyrrolo[3,4-d]pyrimidin-6-yl)ethan-1-one (Target Compound I-2R)

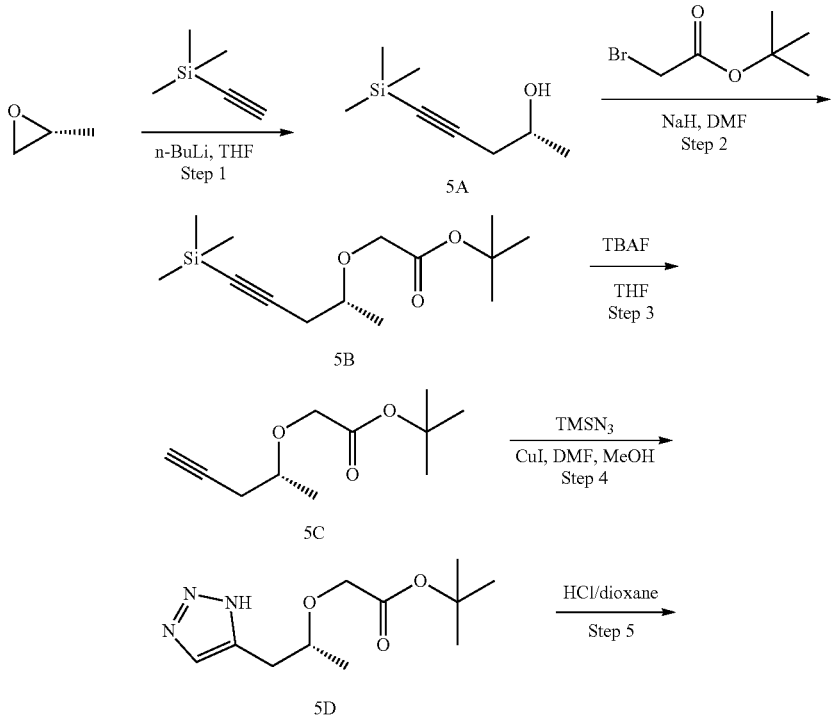

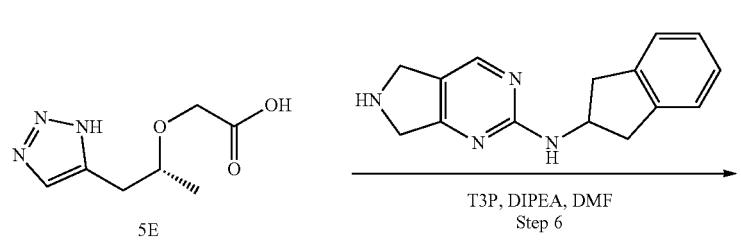

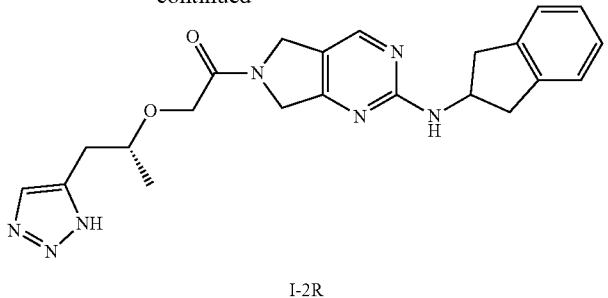

I-2R

Step 1: Synthesis of (R)-5-(trimethylsilyl)pent-4-yn-2-ol (5A)

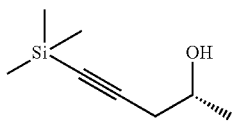

5A

Under nitrogen protection, trimethylsilylacetylene (51.7 g) and diethyl ether (600 mL) were added into a three-necked flask, cooled to −78° C., followed by slowly adding n-butyllithium (2.5 M, 217 mL) dropwise. After the dropwise addition was complete, the mixture reacted for 1 hour while holding the temperature at −78° C., then added with a tetrahydrofuran solution of boron trifluoride (50%, 30 mL), and slowly added with (R)-propylene oxide (30 g) dropwise. After the dropwise addition was complete, the temperature was held while stirring for 1 hour, and a saturated aqueous solution of sodium bicarbonate (300 mL) was added to quench the reaction. The reaction solution, after being heated to room temperature, was separated into layers, and the organic phase was dried, mixed with silica gel, and then separated and purified by a silica gel column (petroleum ether:ethyl acetate (V/V)=10:1) to obtain a product of light-yellow liquid compound, (R)-5-(trimethylsilyl)pent-4-yn-2-ol (34 g, yield 42.1%).

Step 2: Synthesis of tert-butyl (R)-2-((5-(trimethylsilyl)pent-4-yn-2-yl)oxy)acetate (5B)

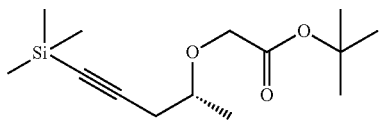

5B

The raw material (R)-5-(trimethylsilyl)pent-4-yn-2-ol (34 g, 218 mmol) was added to 340 mL of dry tetrahydrofuran, and cooled to 0° C., followed by adding 60% NaH (10.44 g, 261 mmol), stirring for 30 min, and adding with a raw material tert-butyl 2-bromoacetate (46.7 g, 239 mmol) at 0° C. The mixture was naturally warmed to room temperature, and stirred for 16 h. At 0° C., the reaction solution was added with methanol (20 mL), mixed with silica gel, concentrated, and separated and purified by a silica gel column (petroleum ether:ethyl acetate (V/V)=10:1) to obtain a light-yellow liquid compound tert-butyl (R)-2-((5-(trimethylsilyl)pent-4-yn-2-yl)oxy)acetate (5B) (50 g, yield 85%).

Step 3: Synthesis of tert-butyl (R)-2-(pent-4-yn-2-yloxy)acetate (5C)

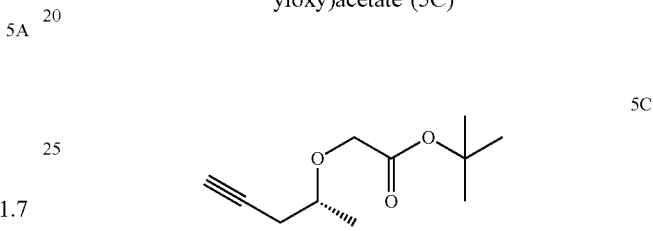

5C

At room temperature, the raw material tert-butyl (R)-2-((5-(trimethylsilyl)pent-4-yn-2-yl)oxy)acetate (50 g, 185 mmol) was added to 500 mL of tetrahydrofuran, and then tetrabutylammonium fluoride (53.2 g, 203 mmol) was added. The mixture reacted at room temperature for 15 h, mixed with silica gel, and concentrated. The residue was separated and purified with a silica gel column (petroleum ether:ethyl acetate (V/V)=10:1) to obtain the title yellow liquid compound tert-butyl (R)-2-(pent-4-yn-2-yloxy)acetate (27 g, 73.7%).

Step 4: Synthesis of tert-butyl (R)-2-((1-(1H-1,2,3-triazol-5-yl)propan-2-yl)oxy)acetate (5D)

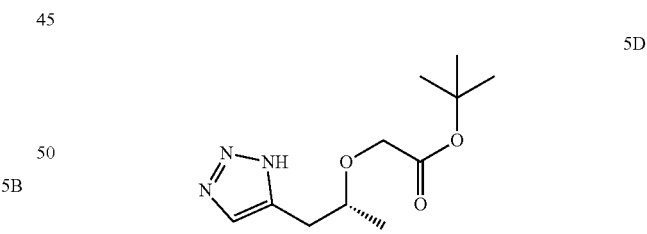

5D

The raw material tert-butyl (R)-2-(pent-4-yn-2-yloxy)acetate (27 g, 136 mmol) was added to 150 mL of DMF and 20 mL of methanol at room temperature. Then, under the nitrogen protection, trimethylsilyl azide (23.53 g, 204 mmol) and cuprous iodide (2.08 g, 10.89 mmol) were added respectively. The reaction solution was heated to 90° C. and stirred for 15 h. The reaction solution was then cooled to 40° C., concentrated to dryness, diluted with dichloromethane, mixed with silica gel, and concentrated. The residue was separated and purified with a silica gel column (petroleum ether:ethyl acetate (V/V)=1:1) to obtain a yellow oily compound tert-butyl (R)-2-((1-(1H-1,2,3-triazol-5-yl)propan-2-yl)oxy)acetate (14 g, 42.6%).

Step 5: Synthesis of (R)-2-((1-(1H-1,2,3-triazol-5-yl)propan-2-yl)oxy)acetic acid (5E)

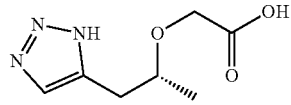

The raw material tert-butyl (R)-2-((1-(1H-1,2,3-triazol-5-yl)propan-2-yl)oxy)acetate (14 g, 58 mmol) was added to a hydrogen chloride solution of 1,4-dioxane (4 mol/L, 70 mL) at room temperature, stirred at room temperature for 16 h, and filtered. The solid was washed with methyl tert-butyl ether, and dried to obtain a white solid (R)-2-((1-(1H-1,2,3-triazol-5-yl)propan-2-yl)oxy)acetic acid (9.2 g, 86%).

Step 6: Synthesis of (R)-2-((1-(1H-1,2,3-triazol-5-yl)propan-2-yl)oxy)-1-(2-((2,3-dihydro-1H-inden-2-yl)amino)-5,7-dihydro-6H-pyrrolo[3,4-d]pyrimidin-6-yl)ethan-1-one (Target Compound I-2R)

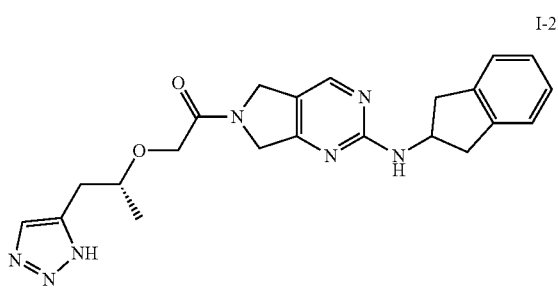 [SMILES: CC(Cc1cnn[nH]1)OCC(=O)N1Cc2cnc(NC3Cc4ccccc4C3)nc2C1]

The raw materials (R)-2-((1-(1H-1,2,3-triazol-5-yl)propan-2-yl)oxy)acetic acid (9.41 g, 42.5 mmol) and N-(2,3-dihydro-1H-inden-2-yl)-6,7-dihydro-5H-pyrrolo[3,4-d]pyrimidine-2-amine (9.2 g, 28.3 mmol) were added to 1,000 mL of DMF, followed by adding T3P (50% DMF solution) (27 g, 42.5 mmol) and diisopropylethylamine (21.95 g, 170 mmol) at 0° C. The mixture was warmed naturally to room temperature and stirred for 16 h. The reaction solution was filtered, and the filtrate was added with water (3 mL) and concentrated to dryness. The residue was separated and purified with a silica gel column (dichloromethane:methanol (V/V)=10:1) to obtain 12 g of crude product. The crude product was beaten with 120 mL of isopropyl acetate for 10 h, and filtered, and dried to obtain (R)-2-((1-(1H-1,2,3-triazol-5-yl)propan-2-yl)oxy)-1-(2-((2,3-dihydro-1H-inden-2-yl)amino)-5,7-dihydro-6H-pyrrolo[3,4-d]pyrimidin-6-yl)ethan-1-one (7.8 g, yield 65.7%).

$^1$H NMR (400 MHz, DMSO-d6) δ 8.30 (d, 1H), 7.64 (b, 1H), 7.57 (t, 1H), 7.22-7.20 (m, 2H), 7.16-7.12 (m, 2H), 4.65-4.59 (m, 3H), 4.52 (s, 1H), 4.42 (s, 1H), 4.25-4.17 (m, 2H), 3.87-3.81 (m, 1H), 3.27-3.21 (m, 2H), 2.90-2.85 (m, 4H), 1.19 (t, 3H)

LC-MS, M/Z (ESI): 420.4(M+1)

Example 7: Preparation of Target Compound I-2S and Target Compound I-2R

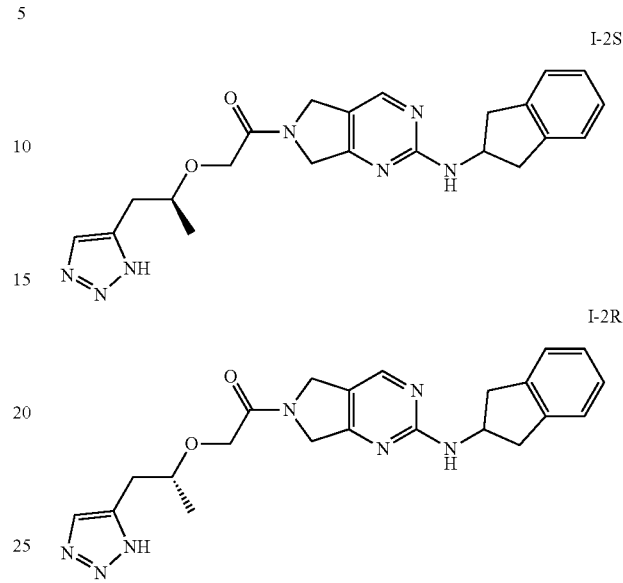

The target compounds were obtained by HPLC separation.

The racemate 2-((1-(1H-1,2,3-triazol-5-yl)propan-2-yl)oxy)-1-(2-((2,3-dihydro-1H-inden-2-yl)amino)-5,7-dihydro-6H-pyrrolo[3,4-d]pyrimidin-6-yl)ethan-1-one (22 g, 52.5 mmol) was separated with HPLC under the following separation conditions: column type: Chiralpak ID (ID00CD-QG003) 4.6 mm, I.D. ×15 cm L; mobile phase: 100% methanol; flow rate: 1.0 mL/min; wavelength: 254 nm; column temperature: 35° C.; back pressure: 10 MPa. The compounds in one single configuration were obtained, and recorded as peak 1 (7.0 g, 100% ee, yield 63.6%) and peak 2 (9.9 g, 97% ee, yield 90.0%), respectively.

By comparing the retention time of the SFC analysis, it was determined that two absolute configurations of the compound were obtained by HPLC resolution.

Target Compound I-2S:
SFC analysis: column type: Chiralpak AY-3 50×4.6 mm I.D., 3 μm; mobile phase: ethanol (containing 0.05% diethylamine); gradient elution: 60% ethanol in $CO_2$ (containing 0.05% diethyl amine); flow rate: 3.0 mL/min; wavelength: 254 nm; column temperature: 35° C.; back pressure: 100 Bar;
Retention time: 0.964 min.

Target Compound I-2R:
SFC analysis: column type: Chiralpak AY-3 50×4.6 mm ID, 3 μm; mobile phase: ethanol (containing 0.05% diethylamine); gradient elution: 60% ethanol in $CO_2$ (containing 0.05% diethylamine); flow rate: 3.0 mL/min; wavelength: 254 nm; column temperature: 35° C.; back pressure: 100 Bar;
Retention time: 2.118 min.

Through the same SFC analysis, the retention time at peak 1 was 1.006 min, and the retention time at peak 2 was 2.205 min. Through the comparison of retention time, it was determined that the peak 1 corresponds to the compound I-2S, i.e., (S)-2-((1-(1H-1,2,3-triazol-5-yl)propan-2-yl)oxy)-1-(2-((2,3-dihydro-1H-inden-2-yl)amino)-5,7-dihydro-6H-pyrrolo[3,4-d]pyrimidin-6-yl)ethan-1-one, and peak 2 corresponds to the compound I-2R, i.e., (R)-2-((1-(1H-1,2,3-triazol-5-yl)propan-2-yl)oxy)-1-(2-((2,3-dihydro-1H-inden-2-yl)amino)-5,7-dihydro-6H-pyrrolo[3,4-d]pyrimidin-6-yl)ethan-1-one.

Example 8: Control Compound and Preparation Thereof

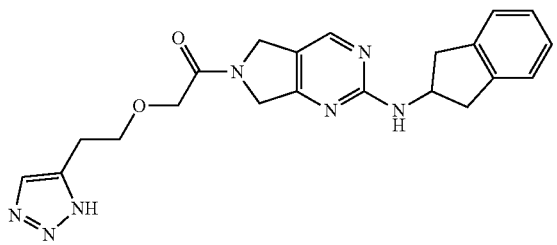 [SMILES: O=C(COCCc1cnn[nH]1)N1Cc2cnc(NC3Cc4ccccc4C3)nc2C1]

Control Compound

The control compound was synthesized in accordance with Patent Application WO2014110000A1.

The control compound in the test examples below is the compound mentioned in Example 8

Test Example 1: Autotaxin (ATX) Enzyme Activity Inhibition Assay

The inhibitory activities of the compounds on the autotaxin enzyme were detected using the Autotaxin Inhibitor Screening Assay Kit (Cayman, 700580). First, the test compound was prepared as a 10 mM stock solution in DMSO solvent, and then the stock solution was diluted with DMSO to 8 gradient concentrations. Subsequently, the 8 concentrations were diluted with Autotaxin Assay buffer (1×) provided in the kit into 19× compound working solutions (DMSO content was 1.9%). The Autotaxin Assay Reagent (10×) was taken out and diluted by 10 times with Autotaxin Assay Buffer (1×). The Autotaxin Substrate was taken out, dissolved by adding 1.2 mL of Autotaxin Assay Buffer (1×), mixed evenly and stood at room temperature. In a 96-well plate, 150 μL of Autotaxin Assay Buffer (1×), 10 μL of the prepared and diluted 19× compound working solutions, 10 μL of Autotaxin Assay Reagent (1×), and 20 μL of the dissolved Autotaxin Substrate were added to each of the wells for each concentration, and homogenously mixed. The 96-well plate was shaken in a constant temperature shaker at 37° C. and incubated in the dark for 30 min, and then the plate was taken out and placed on a microplate reader to read OD405. The experimental results were input into GraphPad Prism software, and the IC$_{50}$ of each compound was calculated by fitting.

TABLE 1

Results of inhibitory activities of the test compounds on ATX activity

| Test compound | IC$_{50}$ (nM) |
|---|---|
| Control compound | 2.60 |
| Compound I-1 | 4.24 |
| Compound I-1R | 2.67 |
| Compound I-1S | 28.6 |

TABLE 1-continued

Results of inhibitory activities of the test compounds on ATX activity

| Test compound | IC$_{50}$ (nM) |
|---|---|
| Compound I-2 | 1.35 |
| Compound I-2S | 1.40 |
| Compound I-2R | 1.59 |

Experimental results reveal that the compounds of the present disclosure have a good inhibitory activity on ATX enzyme, and can effectively inhibit the ATX enzyme activity.

Test Example 2: Human Liver Microsome Stability Test

The human liver microsome stability test was performed by incubating the compound and human liver microsomes in vitro. First, the test compound is prepared as a 10 mM stock solution in DMSO solvent, and then the compound was diluted to 0.5 mM with acetonitrile. Human liver microsomes (Corning) were diluted with PBS and prepared as a microsome/buffer solution, which was used to dilute 0.5 mM of the compound into a working solution. In the working solution, a concentration of the compound was 1.5 μM, and a concentration of human liver microsomes was 0.75 mg/ml. A deep-well multiwell plate was taken, 30 μL of the working solution and 15 μL of pre-warmed NADPH solution (6 mM) were sequentially added to each well to initiate a reaction, and the reaction was incubated at 37° C. At 0, 5, 15, 30, and 45 min of the incubation, 135 μL of acetonitrile was added to the corresponding wells to terminate the reaction. After the reaction was terminated with acetonitrile at the last time point of 45 min, the deep-well plate was vortexed for 10 min (600 rpm/min), and then centrifuged for 15 min. After centrifugation, the supernatant was collected, and added with purified water in a ratio of 1:1 to perform LC-MS/MS detection. Accordingly, a ratio of a peak area of compound to a peak area of internal standard at each time point was obtained, and the peak area ratios of the compound at 5, 15, 30, and 45 min were compared with the peak area ratio at 0 min to calculate the remaining percentage of the compound at each time point. $T_{1/2}$ was calculated by using Excel.

TABLE 2

Results of human liver microsome stability test

| Compound | Remaining percentage (%) of compound after incubation for 30 min | $T_{1/2}$ (min) |
|---|---|---|
| Control compound | 41.2 | 24.1 |
| Compound I-1 | 87.4 | |
| Compound I-1R | 86.0 | 123 |
| Compound I-2S | 42.9 | 26.6 |
| Compound I-2R | 63.7 | 53.6 |

Compared with the control compound, the compounds of the present disclosure exhibited better liver metabolic stability, and they were metabolized more slowly in the human body, and had a higher exposure amount. $T_{1/2}$ of the liver microsome stability of the compounds of the present disclosure is better than that of the control compound, and can even reach twice as much as that of the control compound. Accordingly, the clinical dosage and frequency of administration can be reduced, the toxic and side effects of clinical administration can be lowered, and the clinical compliance was improved.

Test Example 3: Detection of Inhibitory Effect of Compounds on hERG by Using Full-Automatic Electrophysiological Patch Clamp QPatch Full-automatic electrophysiological patch clamp QPatch was used to detect the inhibitory effect of compounds on hERG. Cells used in this test were CHO cell line transfected with cDNA of hERG and stably expressing hERG channels (provided by Sophion Bioscience, Denmark), and the cell passage number was P24. The cells were cultured in a medium containing the following components (all purchased from Invitrogen): Ham's F12 medium, inactivated fetal bovine serum (10% (v/v)), hygromycin B (100 μg/ml), and Geneticin (100 μg/ml). CHO hERG cells were grown in a petri dish containing the above-mentioned medium and cultured in an incubator at 37° C. and containing 5% $Co_2$.

An extracellular fluid (2 mM $CaCl_2$, 1 mM $MgCl_2$, 4 mM KCl, 145 mM NaCl, 10 mM Glucose, 10 mM HEPES, pH: about 7.4, osmotic pressure: about 305 mOsm) and an intracellular fluid (5.374 mM $CaCl_2$, 1.75 mM $MgCl_2$, 120 mM KCl, 10 mM HEPES, 5 mM EGTA, 4 mM Na-ATP, pH about 7.25, osmotic pressure about 295 mOsm) were prepared.

The compound to be tested was prepared as a 10 mM stock solution in DMSO solvent, the compound was diluted to 3 mM, 1 mM, 0.3 mM, and 0.1 mM with DMSO, and then the compound was diluted to 30 μM, 10 μM, 3 μM, 1 μM, 0.3 μM and 0.1 μM with the extracellular fluid, so that except that the final concentration of DMSO in the 30 μM compound was 0.3%, the final concentration of DMSO in compound solutions of all other concentrations was 0.1%.

The CHO hERG cells, after being digested and resuspended, were added to the fully automated QPatch system (Sophion, Denmark), and subjected to a test according to the following preset procedure.

After reaching the ruptured whole cell configuration state in the initial stage, the whole cell current was recorded at room temperature (about 25° C.), and the cells were recorded for at least 120 seconds in order to achieve stability. The stable cells were selected for the test. During the whole test, the cell patch clamp was at a voltage of −80 mV, the cell patch clamp voltage was depolarized to +20 mV to activate the hERG potassium channels, and after 2.5 seconds, the cell patch clamp voltage was at −50 mV to eliminate inactivation and generate outward tail current. The peak tail current was used as the value of the hERG current. The voltage mode described above was applied to the cells for electrophysiological tests every 15 seconds. An intracellular liquid containing 0.1% dimethyl sulfoxide (solvent) was added to the cells to establish a baseline, and then the current was allowed to stabilize for 3 min. After the compound solution was added, the cells were kept in the test environment until the effect of the compound reached a steady state or until reaching 4 min. In the test experiments with different concentration gradients of the compound, the compound was added to the clamped cells from low to high concentration. After the compound test was finished, the cells were washed with the extracellular fluid until the current returned to a stable state.

The test data were analyzed by Qpatch analysis software provided by Sophion, Excel, and Graphpad Prism.

TABLE 3

Results of inhibitory effects of compounds on hERG

| Compound | hERG $IC_{50}$ (μM) | hERG $IC_{50}$/ATX $IC_{50}$ |
| --- | --- | --- |
| Control compound | 6.69 | 6.69/2.60 = 2.6 |
| Compound I-1 | 22.3 | 22.3/4.24 = 5.26 |
| Compound I-1R | 22.0 | 22.0/2.67 = 8.24 |
| Compound I-2S | 8.78 | 8.87/1.40 = 6.3 |
| Compound I-2R | 9.48 | 9.48/1.59 = 6.0 |

Compared with the control compound, the compounds of the present disclosure exhibit weaker inhibitory activity on hERG. Taking the $IC_{50}$ value of the compounds for indicating the inhibition of ATX enzyme activity into consideration, the compounds of the present disclosure exhibit a favorable safety window for hERG inhibition, and had significant cardiac safety advantages.

Test Example 4: Thermodynamic Solubility Test

Prepared were phosphate buffered saline (PBS, pH 7.4), FeSSIF solution (pH 5.8, containing 10 mM sodium taurocholate, 2 mM lecithin, 81.65 mM sodium hydroxide, 125.5 mM sodium chloride, 0.8 mM sodium oleate, 5 mM glyceryl monooleate, 55.02 mM maleic acid), and FaSSGF solution (pH 1.6, 1 L solution containing 80 μM sodium taurocholate, 20 μM lecithin, 0.1 g pepsin, and 34.2 mM sodium chloride).

The compound was accurately weighed, and the prepared phosphate buffer (pH 7.4), FeSSIF solution (pH 5.8) and FaSSGF solution (pH 1.6) were added to prepare a solution with a concentration of 4 mg/mL, which was shaken at 1,000 rpm for 1 hour, and then incubated overnight at room temperature. After the incubation, the solution was centrifuged at 12,000 rpm for 10 min to remove undissolved particles, and the supernatant was transferred to a new centrifuge tube. The supernatant was diluted appropriately, then added with an acetonitrile solution containing the internal standard, and quantified using a standard curve prepared with the same matrix.

TABLE 4

Results of thermodynamic solubility test

| | Dissolubility (μg/mL) | | |
| --- | --- | --- | --- |
| Test compound | FaSSGF (pH 1.6) | FeSSIF (pH 5.8) | PBS (pH 7.4) |
| Control compound | 66.5 | 18.3 | 6.3 |
| Compound I-1R | 88.5 | 20.4 | 20.4 |
| Compound I-2S | 1240 | | 73.6 |
| Compound I-2R | 1037 | 260 | 107 |

The experimental results indicate that the solubility of the control compound is relatively poor, and thus the absorption of the gastrointestinal tract is supposed to be relatively poor, which is not conducive to the development of medicaments for oral administration. Compared with the control compound, the thermodynamic solubility of the compounds of the present disclosure in simulated gastric juice, simulated intestinal juice, and neutral conditions is significantly improved. Accordingly, it is expected that the intestinal absorption in the human body will be greatly improved, and the oral administration exposure will be higher, such that the clinical administration dose can be reduced and clinical compliance can be improved.

Test Example 5: Pharmacokinetic Test

For the in vivo pharmacokinetic test of rats, 6 male SD rats were used, 180-240 g, fasted overnight. Three of the rats were orally administered by gavage (10 mg/kg), and blood was collected before the administration, and at 15 min, 30 min, 1 h, 2 h, 4 h, 8 h and 24 h after the administration. The other 3 rats were intravenously administered with the compound (1 mg/kg), and blood was collected before the administration, and at 5 min, 15 min, 30 min, 1 h, 2 h, 4 h, 8 h and 24 h after the administration. The blood samples were centrifuged at 8,000 rpm at 4° C. for 6 min, and plasma was collected and stored at −20° C. The plasma at each time point was taken and added with an acetonitrile solution containing internal standard in 3-5 times the amount, vortexed and mixed for 1 min, and centrifuged at 13,000 rpm at 4° C. for 10 min. The supernatant was collected, added and mixed with water in 3 times the amount. An appropriate amount of the mixture was taken for LC-MS/MS analysis. The main pharmacokinetic parameters were analyzed using WinNonlin 7.0 software with non-compartmental model.

For the in vivo pharmacokinetic test of mice, 18 male ICR mice were used, 20-25 g, fasted overnight. Among them, 9 mice were orally administered by gavage (10 mg/kg), bloods of 3 mice were collected at each blood collection time point, and the bloods of the 9 mice were alternately collected. The other 9 mice were intravenously administered with the compound (1 mg/kg), bloods of 3 mice were collected at each blood collection time point, and the bloods of the 9 mice were alternately collected. The rest operations were the same as that of pharmacokinetic test in rats.

The experimental results indicate that, compared with the control compound, the compounds of the present disclosure exhibit better pharmacokinetic properties. Especially in rats, a clearance rate (CL) of the compound I-2R of the present disclosure is much lower, which is about ¼ that of the control compound, indicating that this compound is relatively stable in the body, and its oral $C_{max}$ and $AUC_{0-t}$ can reach 6.1 times and 4.2 times that of the control compound, respectively.

Test Example 6: Inhibition Test of ATX Enzyme Activity in Human Plasma

Whole blood was collected from healthy volunteers and anticoagulated with heparin. The blood collection tubes were centrifuged at 3,000 rpm for 10 min, and the plasma was taken and stored at −80° C. for use.

The compound was serially diluted with DMSO according to the conventional concentration requirements, and then 3 μL of the diluted compound was added to a 96-well plate, and 147 μL of PBS was added to each well containing 3 μL of the compound. After mixing homogenously, 50 μL of the mixture was removed and added to a new 96-well plate. The human plasma was taken out from the −80° C. refrigerator and thawed through rapid shaking in a 37° C. water bath. 50 μL of the human plasma was taken and added to the 96-well plate containing 50 μL of the diluted compound (the final

TABLE 5

Results of pharmacokinetic test in mice

In vivo pharmacokinetics parameters in mice

| Test compound | Intravenous administration (1 mg/kg) | | | | Oral administration by gavage (10 mg/kg) | | | |
|---|---|---|---|---|---|---|---|---|
| | CL (L/h/kg) | Vz (L/kg) | AUC0-t (h*ng/ml) | $T_{1/2}$ (h) | Cmax (ng/ml) | Tmax (hr) | AUC0-t (h*ng/ml) | $T_{1/2}$ (h) |
| Control compound | 3.45 | 1.67 | 290 | 0.34 | 2042 | 0.25 | 2902 | 0.83 |
| Compound I-1R | 2.09 | 1.05 | 495 | 0.37 | 6939 | 0.42 | 6123 | 0.67 |
| Compound I-2R | 1.60 | 0.88 | 626 | 0.38 | 6357 | 0.25 | 6368 | 0.87 |

TABLE 6

Results of pharmacokinetic test in rats

In vivo pharmacokinetics parameters in rats

| Test compound | Intravenous administration (1 mg/kg) | | | | Oral administration by gavage (10 mg/kg) | | | |
|---|---|---|---|---|---|---|---|---|
| | CL (L/h/kg) | Vz (L/kg) | AUC0-t (h*ng/ml) | $T_{1/2}$ (h) | Cmax (ng/ml) | Tmax (hr) | AUC0-t (h*ng/ml) | $T_{1/2}$ (h) |
| Control compound | 1.76 | 1.12 | 580 | 0.45 | 2591 | 0.42 | 4874 | 1.31 |
| Compound I-1R | 1.28 | 0.76 | 828 | 0.43 | 3394 | 0.5 | 6333 | 2.51 |
| Compound I-2S | 1.51 | 0.74 | 661 | 0.34 | 2416 | 0.42 | 3688 | 1.91 |
| compound I-2R | 0.28 | 0.21 | 3648 | 0.50 | 15844 | 0.33 | 20675 | 2.56 | system was 1% DMSO). The group without the compound was set as the positive control group. The 96-well plate was shaken and mixed uniformly, and incubated at 37° C. for 3 h. A blank group was also provided, and the plasma of the blank group was stored at −80° C. The blank group is provided to determine the baseline concentration of endogenous LPA.

After the incubation was finished, the blank group was thawed on ice and transferred to an incubation plate. Excess acetonitrile containing the internal standard LPA17:0 was added to the incubation plate to precipitate the plasma protein. After vortex centrifugation, the supernatant was taken and diluted, and a peak area of LPA18:2 and a peak area of internal standard LPA17:0 were detected using LC-MSMS mass spectrometry.

A ratio of the peak area of LPA18:2 to the peak area of internal standard LPA17:0 was calculated, and a formation inhibition rate of LPA18:2 was calculated according to the following formula:

Inhibition rate (%)=100−(compound group with different concentration−blank group)/(positive control group−blank group)*100

According to the inhibition rates of different concentrations of the compound, the IC$_{50}$ value of the compound, which is related to inhibition of ATX enzyme activity in human plasma, was calculated.

TABLE 7

Results of inhibitory effects of test compounds on ATX enzyme activity in human plasma

| Test compound | IC$_{50}$ (nM) |
|---|---|
| Control compound | 13.0 |
| Compound I-1R | 12.0 |
| Compound I-2S | 2.1 |
| Compound I-2R | 4.73 |

Experimental results show that the compounds of the present disclosure have good inhibitory activity on ATX enzyme in human plasma, can effectively inhibit ATX enzyme activity, and are significantly better than the control compound.

Test Example 7: IPF Model Induced by Bleomycin in Rats

Using male BN rats, 180-240 g, idiopathic pulmonary fibrosis model (IPF model) was induced with a dose of 5 U/kg bleomycin. After the model was established, the animals were randomly divided into groups, including a solvent control group, a GLPG-1690 group (Galapagos clinical phase III compound), a control compound group, a compound I-2S group, and a compound I-2R group. On the second day after the model was established, the animals were orally administered by gavage twice a day, where the administration group was administered with a dose of 30 mg/kg each time, and the solvent control group was administered with a blank solvent, and the administration continued for 21 days.

During the administration, the body weight was weighed every three days. On day 21 of administration, alveolar lavage was conducted 2 h after the first administration, and the inflammatory cells in the lavage fluid were counted, and the associated biomarkers in the supernatant of the lavage fluid were detected. After lavage, the left lungs of the rats were fixed, and stained with Masson's trichrome staining to score the fibrosis pathology. The remaining lung lobes were cryopreserved. The supernatant of the alveolar lavage fluid and the freshly frozen lung tissue of the three compound groups were taken and detected for a content of TGF-β1 protein and an amount of total protein by using ELISA, and the amount of TGF-β1 per milligram of total protein was calculated.

Figure 2:
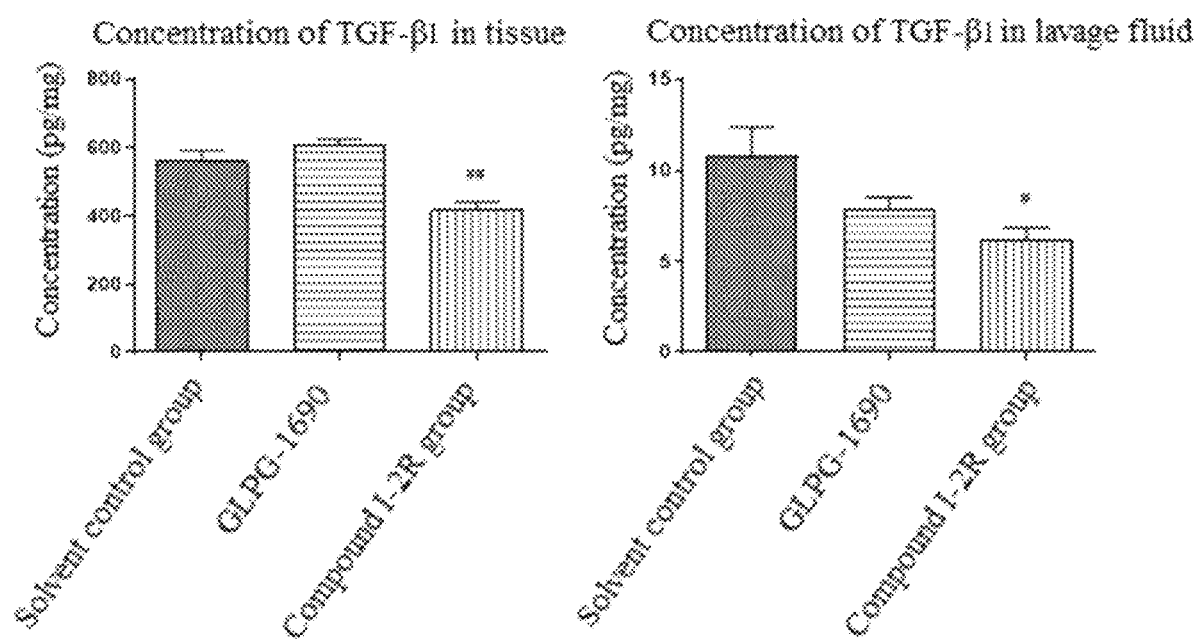
FIG. 2 is a diagram illustrating changes in concentrations of TGF-β1 in lung tissue and bronchoalveolar lavage fluid after administration according to an embodiment of the present disclosure.

The experimental results indicate that the weight reductions of the animals from the compound I-2S and compound I-2R groups were significantly less than that of the control compound group, and the compounds of the present disclosure have better safety (the results are illustrated in FIG. 1); the contents of TGF-β1 in the supernatant of the alveolar lavage fluid and the freshly frozen lung tissue of the compound I-2R group are significantly lower than those of the solvent control group, and thus the compound of the present disclosure has a significant anti-fibrosis effect (the results are shown in FIG. 2).

In the specification, descriptions with reference to the terms "an embodiment", "some embodiments", "examples", "specific examples", or "some examples", etc. mean specific features, structures, materials or characteristics described in conjunction with the embodiment or example are included in at least one embodiment or example of the present disclosure. In this specification, the above terms are illustrative, and do not necessarily refer to the same embodiment or example. Moreover, the described specific features, structures, materials or characteristics can be combined in a suitable manner in any one or more embodiments or examples. In addition, those skilled in the art can combine the different embodiments or examples and the features of the different embodiments or examples described in this specification without contradicting each other.

Although the embodiments of the present disclosure are illustrated and described above, it can be understood that the above-mentioned embodiments are illustrative and should not be construed as limitations of the present disclosure. Those skilled in the art can make changes, modifications, substitutions, and variations based on the above-mentioned embodiments within the scope of the present disclosure.

What is claimed is:

1. A compound, being a compound represented by Formula I; or being a tautomer, a stereoisomer, a hydrate, a solvate, a salt, or a prodrug of the compound represented by Formula I,

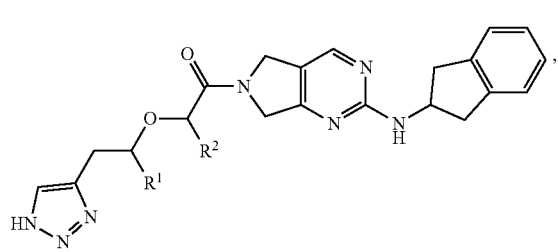

wherein,
R$^1$ and R$^2$ are each independently selected from —H or —CH$_3$,
provided that:
when R$^1$ and R$^2$ are not —H simultaneously; or
when R$^1$ and R$^2$ are not —CH$_3$ simultaneously.

2. The compound according to claim 1, wherein R$^1$ is —H, and R$^2$ is —CH$_3$.

3. The compound according to claim 1, wherein $R^1$ is —$CH_3$, and $R^2$ is —H.

4. The compound according to claim 1, wherein the compound is one of the following compounds; or a tautomer, a stereoisomer, a hydrate, a solvate, a salt, or a prodrug of one of following compounds,

I-1

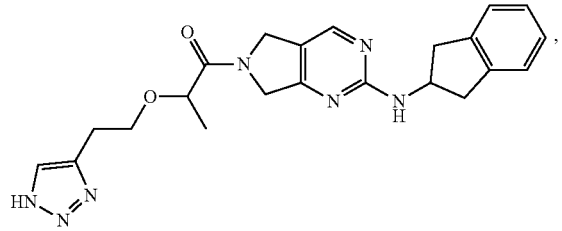

I-2

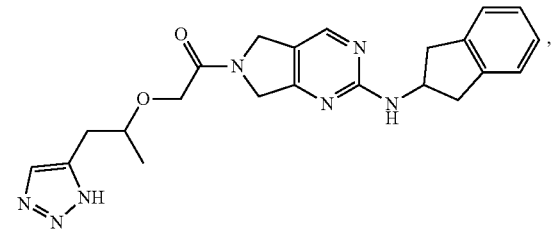

I-1R

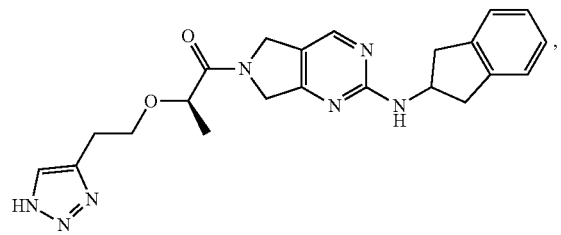

I-1S

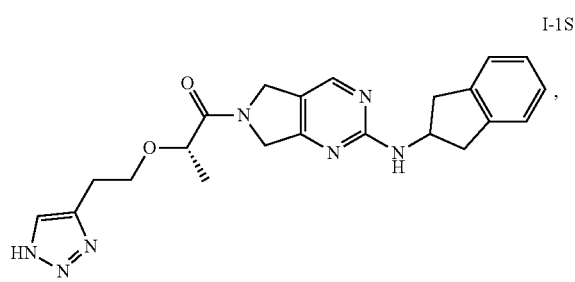

I-2S

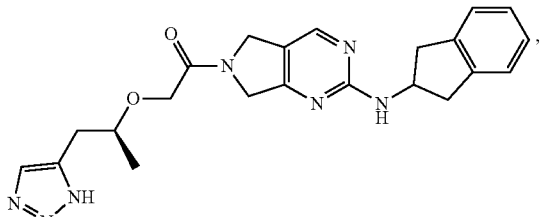

I-2R

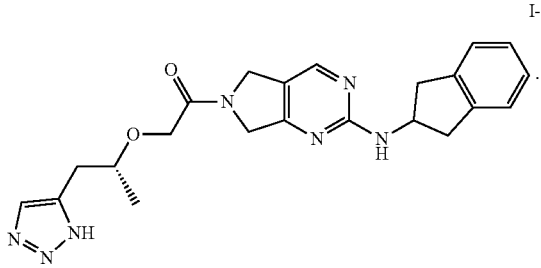

5. A pharmaceutical composition, comprising the compound according to claim 1 as an active ingredient.

6. A drug combination, comprising:
   the compound according to claim 1; and
   an additional drug for treating ATX-related diseases.

7. A method for treating ATX-related diseases, the method comprising:
   administering the compound according to claim 1 to a patient.

8. The method according to claim 7, wherein the ATX-related diseases comprise at least one selected from cancer, metabolic disease, kidney disease, liver disease, fibrosis disease, interstitial lung disease, proliferation disease, inflammatory disease, pain, autoimmune disease, respiratory disease, cardiovascular disease, neurodegenerative diseases, dermatological disorder, and/or abnormal angiogenesis-related disease.

9. The method according to claim 7, wherein the ATX-related diseases comprise at least one selected from interstitial lung disease, pulmonary fibrosis, liver fibrosis, or renal fibrosis.

10. The method according to claim 7, wherein the ATX-related diseases comprise idiopathic pulmonary fibrosis.

11. The method according to claim 7, wherein the ATX-related diseases comprise type II diabetes and nonalcoholic steatohepatitis.

12. The method according to claim 7, wherein the ATX-related diseases comprise neuropathic pain and inflammatory pain.

13. The method according to claim 7, wherein the ATX-related diseases comprise osteoarthritis-related pain.

* * * * *